United States Patent
Dominowski et al.

(10) Patent No.: US 7,122,191 B2
(45) Date of Patent: Oct. 17, 2006

(54) MICROFLUIDIZED OIL-IN-WATER EMULSIONS AND VACCINE COMPOSITIONS

(75) Inventors: Paul Joseph Dominowski, Hickory Corners, MI (US); Pamela K. Klose, East Lyme, CT (US); Richard L. Krebs, Ashland, NE (US); Ramasamy M. Mannan, Kalamazoo, MI (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 11/096,831

(22) Filed: Apr. 1, 2005

(65) Prior Publication Data

US 2005/0220814 A1    Oct. 6, 2005

Related U.S. Application Data

(60) Provisional application No. 60/559,677, filed on Apr. 5, 2004.

(51) Int. Cl.
 *A61K 39/385* (2006.01)
 *A61K 39/295* (2006.01)
 *A61K 45/00* (2006.01)

(52) U.S. Cl. ............ 424/196.11; 424/197.11; 424/201.1; 424/278.1; 424/283.1

(58) Field of Classification Search ............ 424/204.1, 424/196.11, 197.11, 201.1, 278.1, 283.1, 424/184.1, 185.1
See application file for complete search history.

(56) References Cited

U.S. PATENT DOCUMENTS

| | | | |
|---|---|---|---|
| 4,310,550 A | 1/1982 | Wolff, III | 514/776 |
| 4,908,154 A | 3/1990 | Cook | 516/21 |
| 5,084,269 A | 1/1992 | Kullenberg | 424/256.1 |
| 5,376,369 A | 12/1994 | Allison | 424/278.1 |
| 5,679,354 A | 10/1997 | Morein | 424/278.1 |
| 5,690,942 A | 11/1997 | Hjorth | 424/283.1 |
| 5,718,904 A | 2/1998 | Hjorth | 424/278.1 |
| 5,951,988 A | 9/1999 | Littel-van den Hurk | 424/278.1 |
| 5,961,970 A | 10/1999 | Lowell | 424/93.1 |
| 6,080,725 A | 6/2000 | Marciani | 514/26 |
| 6,299,884 B1 | 10/2001 | Van Nest | 424/283.1 |
| 6,506,368 B1 | 1/2003 | Friede | 424/49 |
| 2003/0095974 A1 | 5/2003 | Garcon | |
| 2003/0161834 A1* | 8/2003 | Friede et al. | 424/184.1 |

FOREIGN PATENT DOCUMENTS

| | | |
|---|---|---|
| WO | WO90/14837 | 12/1990 |
| WO | WO96/33739 | 10/1996 |
| WO | WO2004/067031 A1 | 8/2004 |
| WO | WO2004/087204 A2 | 10/2004 |

OTHER PUBLICATIONS

Beer et al., "A new inactivatd BVDV genotype I and II vaccine an immunisation and challenge study with BVDV genotype I," Veterinary Microbioogy, 77, pp. 195-208 (2000).*
Anthony C. Allison, "Squalene and Squalane Emulsions as Adjuvants", Methods 19, 87-93 (1999); SurroMed Corporation, Palo Alto, CA.
Charlotte R. Kensil, et al., "Separation and Caracterization of Saponins with Adjuvant Activity from *Quillaja saponario* Monina Cortex", The Journal of Immunology, vol. 146, 431-437, No. 2 (1991), Cambridge Biotech Corporation, Worcester, MA.

* cited by examiner

*Primary Examiner*—Bruce R. Campell
*Assistant Examiner*—M. Franco Salvoza
(74) *Attorney, Agent, or Firm*—Timothy J. Gumbleton

(57) ABSTRACT

This invention provides submicron oil-in-water emulsions useful as a vaccine adjuvant for enhancing the immunogenicity of antigens. The present invention also provides vaccine compositions containing an antigen combined with such emulsions intrinsically or extrinsically. Methods of preparing the emulsions and vaccines are also provided by the present invention.

8 Claims, 12 Drawing Sheets

MICROFLUIDIZED OIL-IN-WATER EMULSIONS AND VACCINE COMPOSITIONS

CROSS REFERENCE TO RELATED APPLICATIONS

The present application claims priority benefit of U.S. Provisional Patent Application No. 60/559,677, filed Apr. 5, 2004, which is hereby incorporated by reference in its entirety.

FIELD OF INVENTION

This invention relates generally to the field of vaccines and particularly, to adjuvant formulations for enhancing immune response in veterinary animals. In particular, the invention relates to the use of a submicron oil-in-water emulsion as a vaccine adjuvant for enhancing the immunogenicity of antigens. Submicron oil-in-water emulsion formulations, vaccine compositions containing an antigen incorporated into such emulsions, as well as methods of preparing the emulsions and vaccines, are provided by the present invention. The present invention also provides compositions containing complexes formed by a saponin glycoside and a sterol suitable for use in vaccines.

BACKGROUND OF THE INVENTION

Bacterial, viral, parasitic and mycoplasma infections are wide spread in the veterinary animals such as cattle, swine and companion animal. Diseases caused by these infectious agents are often resistant to antimicrobial pharmaceutical therapy, leaving no effective means of treatment. Consequently, a vaccinology approach is increasingly used to control the infectious disease in the veterinary animals. A whole infectious pathogen can be made suitable for use in a vaccine formulation after chemical inactivation or appropriate genetic manipulation. Alternatively, a protein subunit of the pathogen can be expressed in a recombinant expression system and purified for use in a vaccine formulation.

Adjuvant generally refers to any material that increases the humoral and/or cellular immune response to an antigen. The traditional vaccines are composed of crude preparation of killed pathogenic microorganisms, and the impurities associated with the cultures of pathological microorganisms could act as adjuvant to enhance the immune response. However, when homogeneous preparations of pathological microorganisms or purified protein subunits are used as antigens for vaccination, the immunity invoked by such antigens is poor and the addition of certain exogenous materials as adjvuant therefore becomes necessary. Further, synthetic and subunit vaccines are expensive to produce. Therefore, with the aid of adjuvant, a smaller dose of antigen may be required to stimulate the immune response, thereby saving the production cost of vaccines.

Adjuvants are known to act in a number of different ways to enhance the immune response. Many adjuvants modify the cytokine network associated with immune response. These immunomodulatory adjuvants can exert their effect even when they are not together with antigens. In general the immunomodulatory adjuvants cause a general up-regulation of certain cytokines and a concomitant down regulation of others leading to a cellular Th1and/or a humoral Th2 response.

Some adjuvants have the ability to preserve the conformational integrity of an antigen so that the antigens can be efficiently presented to appropriate immune effector cells. As a result of this preservation of antigen conformation by the adjuvant formulation, the vaccine would have an increased shelf-life such as that shown for immune stimulating complexes (ISCOMs). Ozel M.,et.al.; Quarternary Structure of the Immunestimmulating Complex (Iscom), *J. of Ultrastruc. and Molec. Struc. Res.* 102, 240 –248 (1989).

Some adjuvants have the property of retaining the antigen as a depot at the site of injection. As a result of this depot effect the antigen is not quickly lost by liver clearance. Aluminum salts and the water-in-oil emulsions act through this depot effect for a shorter duration. For example, one can obtain a long-term depot by using Freund's complete adjuvant (FCA) which is an water-in-oil emulsion. FCA typically remains at the injection site until biodegradation permits removal of the antigen by antigen-presenting cells.

Based on their physical nature, adjuvants can be grouped under two very broad categories, namely particulate adjvuants and non-particulate adjvuants. Particulate adjuvants exist as microparticles. The immunogen is either able to incorporate or associate with the microparticles. Aluminum salts, water-in-oil emulsions, oil-in-water emulsions, immune stimulating complexes, liposomes, and nano- and microparticles are examples of particulate adjuvants. The non-particulate adjuvants are generally immunomodulators and they are generally used in conjunction with particulate adjuvants. Muramyl dipeptide (an adjuvant-active component of a peptidoglycan extracted from Mycobacteria), non-ionic block copolymers, Saponins (a complex mixture of triterpenoids extracted from the bark of the *Quillaja saponaria* tree), Lipid A (a disaccharide of glucosamine with two phosphate groups and five or six fatty acid chains generally C12 to C16 in length), cytokines, carbohydrate polymers, derivatized polysaccharides, and bacterial toxins such as cholera toxin and *E. coli* labile toxin (LT) are examples of non-particulate adjuvants.

Some of the best-known adjuvants are combination of non-particulate immunomodulators and particulate materials which could impart depot effect to the adjuvant formulation. For example, FCA combines the immunomodualtory properties of *Mycobacterium tuberculosis* components along with the short-term depot effect of oil emulsions.

Oil emulsions have been used as vaccine adjuvant for a long time. Le Moignic and Pinoy found in 1916 that a suspension of killed *Salmonella typhimurium* in mineral oil increased the immune response. Subsequently in 1925, Ramon described starch oil as one of the substances augmenting the antitoxic response to diptheria toxoid. However, the oil emulsions did not become popular until 1937 when Freund came out with his adjuvant formulation now known as Freund's Complete Adjuvant (FCA). FCA is a water-in-oil emulsion composed of mineral (paraffin) oil mixed with killed Mycobateria and Arlacel A. Arlacel A is principally mannide monooleate and is used as an emulsifying agent. Although FCA is excellent in inducing an antibody response, it causes severe pain, abscess formation, fever and granulomatous inflammation. To avoid these undesirable side reactions, Incomplete Freund's Adjuvant (IFA) was developed. IFA is similar to FCA in its composition except for the absence of mycobacterial components. IFA acts through depot formulation at the site of injection and slow release of the antigen with stimulation of antibody-producing cells.

Another approach to improve FCA was based on the notion that replacing the mineral oil with a biocompatible oil would help eliminate the reactions associated with FCA at the injection site. It was also believed that the emulsion should be oil-in-water rather than water-in-oil, because the latter produces a long-lasting depot at the injection site. Hilleman et al. described an oil-based adjuvant "Adjuvant 65", consisting of 86% peanut oil, 10% Arlacel A as emulsifier and 4% aluminum monostearate as stabilizer. Hilleman, 1966, Prog. Med. Virol. 8: 131–182; Hilleman and Beale, 1983, in New Approaches to Vaccine Development (Eds. Bell, R. and Torrigiani, G.), Schwabe, Basel. In humans, Adjuvant 65 was safe and potent but exhibited less adjuvanticity than IFA. Nevertheless, the use of Adjvuant 65 was discontinued due to reactogenicity for man with certain lots of vaccine and reduction in adjuvanticity when a purified or synthetic emulsifier was used in place of Arlacel A. U.S. Pat. Nos. 5,718,904 and 5,690,942 teach that the mineral oil in the oil-in-water emulsion can be replaced with metabolizable oil for the purpose of improving the safety profile.

Besides the adjuvanticity and safety, the physical appearance of an emulsion is also an important commercial consideration. Physical appearance depends on the stability of the emulsion. Creaming, sedimentation and coalescence are indicators of the emulsion instability. Creaming occurs when oil and aqueous phases of the emulsion have different specific gravity. Creaming also occurs when the initial droplet size of the emulsion is large and the emulsion droplets are not having any Brownian motion. When the droplet size is large, there is a tendency for the interfacial rupture and the droplets coalesce into large particles. The stability of the emulsion is determined by a number of factors such as the nature and amount of emulsifier used, the size of the droplet size in the emulsion, and the difference in the density between the oil and water phase.

Emulsifiers promote stabilization of dispersed droplet by reducing the interfacial free energy and creating physical or electrostatic barriers to droplet coalescence. Nonionic as well as ionic detergents have been used as emulsifiers. Nonionic emulsifiers orient at the interface and produce relatively bulky structures, which leads to steric avoidance of the dispersed droplets. Anionic or cationic emulsifiers induce formation of an electrical double layer by attracting counter ions; the double layer repulsive forces cause droplets to repel one another when they approach.

Besides using the emulsifiers, the stability of the emulsion can also be achieved through reducing the droplet size of the emulsion by mechanical means. Typically propeller mixers, turbine rotors, colloid mills, homogenizers, and sonicators have been used to manufacture emulsions. Microfluidization is another way to increase the homogeneity of the droplet size in the emulsion. Microfluidization can produce an elegant, physically stable emulsion with consistent particle size in the submicron range. Besides increasing the stability of the emulsion, the process of microfluidization allows terminal filtration which is a preferred way of ensuring the sterility of the final product. Moreover, submicron oil particles can pass from injection sites into the lymphatics and then to lymph nodes of the drainage chain, blood and spleen. This reduces the likelihood of establishing an oily depot at the injection site which may produce local inflammation and significant injection site reaction.

Microfluidizers are now commercially available. Emulsion formation occurs in a microfluidizer as two fluidized streams interact at high velocities within an interaction chamber. The microfluidizer is air or nitrogen driven and can operate at internal pressures in the excess of 20,000 psi. U.S. Pat. No. 4,908,154 teaches the use of microfluidizer for obtaining emulsions essentially free of any emulsifying agents.

A number of submicron oil-in-water adjuvant formulations have been described in the literature. U.S. Pat. No. 5,376,369 teaches a submicron oil-in-water emulsion adjuvant formulation known as Syntax Adjuvant Formulation (SAF). SAF contains squalene or squalane as the oil component, an emulsion-forming amount of Pluronic L121 (polyoxy-proplyene-polyoxyethylene) block polymer and an immunopotentiating amount of muramyldipeptide. Squalene is a linear hydrocarbon precursor of cholesterol found in many tissues, notably in the livers of sharks and other fishes. Squalane is prepared by hydrogenation of squalene and is fully saturated. Both squalene and squalane can be metabolized and have a good record of toxicological studies. Squalene or squalane emulsions have been used in human cancer vaccines with mild side effects and a desirable efficacy. See, e.g., Anthony C. Allison, 1999, Squalene and Squalane emulsions as adjuvants, *Methods* 19:87 –93.

U.S. Pat. No. 6,299,884 and International Patent Publication WO 90/14837 teach that the polyoxy-proplyene-polyoxyethylene block copolymers are not essential for the formation of submicron oil-in-water emulsion. Moreover, these references teach the use of non-toxic, metabolizable oil and expressly exclude the use of mineral oil and toxic petroleum distillate oils in their emulsion formulations.

U.S. Pat. No. 5,961,970 teaches yet another submicron oil-in-water emulsion to be used as a vaccine adjuvant. In the emulsion described in this patent, the hydrophobic component is selected from the group consisting of a medium chain triglyceride oil, a vegetable oil and a mixture thereof. The surfactant included in this emulsion can be a natural biologically compatible surfactant such as phospholipid (e.g., lecithin) or a pharmaceutically acceptable non-natural surfactant such as TWEEN-80. This patent also teaches incorporating the antigen into the emulsion at the time the emulsion is formed, in contrast to mixing the antigen with the emulsion after the emulsion has been independently and extrinsically formed.

U.S. Pat. No. 5,084,269 teaches that an adjuvant formulation containing lecithin in combination with mineral oil causes a decrease in irritation within the host animal and simultaneously induces increased systemic immunity. The adjuvant formulation resulting from U.S. Pat. No. 5,084,269 is commercially used in veterinary vaccines under the trade name AMPHIGEN®. The AMPHIGEN® formulation is made up of micelles—oil droplets surrounded by lecithin. These micelles allow more whole cell antigens to attach than traditional oil-based adjuvants. Moreover, the AMPHIGEN® based vaccine formulations contain a low oil content of 2.5 to 5% mineral oil, compared to other vaccine formulations containing oil adjuvants, which typically contain from 10% to 20% oil. Its low oil content makes this adjuvant-based vaccine formulation less irritating to tissues at the injection site, resulting in fewer lesions and less trim at slaughter. In addition, the lecithin coating surrounding the oil droplets further reduces injection site reactions resulting in a vaccine that is both safe and efficacious.

The AMPHIGEN® formulation is used as an adjuvant in a number of veterinary vaccines and there is need to maintain the physical appearance of the vaccine product during short and long storage periods as well as at the time of reconstitution. In addition, a lyophilized antigen is mixed with the pre-made adjuvant formulation just before the injection. This practice does not always ensure that there is a uniform distribution of the antigen within the oil-in-water emulsion and the appearance of the emulsion may not be desirable. Moreover, upon standing, the homogenized emulsion can show phase separation. Therefore, there exists a need for a stable adjuvant formulation which does not show phase separation upon long shelf-life. One way to prevent the phase separation is to reduce the droplet size and increase the particle homogeneity of the emulsion. While the process of microfluidization of metabolizable oil-based emulsion formulations has been documented, microfluidization of oil-in-water emulsions such as the AMPHIGEN® formulation has not yet been carried out.

In the present invention, microfluidization has been used to bring the size of lecithin-surrounded mineral oil droplets to submicron size. Unexpectedly, it has been discovered by the present inventors that microfluidization of vaccine formulations adjuvanted with an oil-in-water emulsion comprised of a mixture of lecithin and oil not only improves the physical appearance of the formulations, but also enhances the immunizing effects of the formulations. Microfluidized formulations are also characterized by an improved safety profile.

SUMMARY OF THE INVENTION

It has been unexpectedly discovered by the present inventors that the adjuvant activity and the safety profile of non-metabolizable oil based oil-in-water emulsions can be improved through microfluidization. Antigens incorporated in microfluidized emulsions are stable even when the antigens are intrinsically incorporated into the emulsions prior to microfluidization.

Accordingly, in one embodiment, the present invention provides submicron oil-in-water emulsion formulations useful as a vaccine adjuvant. The submicron oil-in-water emulsions of the present invention are composed of a non-metabolizable oil, at least one surfactant, and an aqueous component, where the oil is dispersed in the aqueous component with an average oil droplet size in the submicron range. A preferred non-metabolizable oil is light mineral oil. Preferred surfactants include lecithin, TWEEN®-80 and SPAN®-80.

A preferred oil-in-water emulsion provided by the present invention is composed of an AMPHIGEN® formulation.

The oil-in-water emulsions of the present invention can include additional components that are appropriate and desirable, including preservatives, osmotic agents, bioadhesive molecules, and immunostimulatory molecules. Preferred immunostimulatory molecules include, e.g., Quil A, cholesterol, GPI-0100, dimethyldioctadecylammonium bromide (DDA).

In another embodiment, the present invention provides methods of preparing a submicron oil-in-water emulsion. According to the present invention, the various components of the emulsion, including oil, one or more surfactants, an aqueous component and any other component appropriate for use in the emulsion, are mixed together. The mixture is subjected to a primary emulsification process to form an oil-in-water emulsion, which is then passed through a microfluidizer to obtain an oil-in-water emulsion with droplets of less than 1 micron in diameter, preferably with a mean droplet size of less than 0.5 micron.

In still another embodiment, the present invention provides vaccine compositions which contain an antigen and a submicron oil-in-water emulsion described hereinabove. The antigen is incorporated into the emulsion either extrinsically or intrinsically, preferably, intrinsically.

The antigen which can be included in the vaccine compositions of the present invention can be a bacterial, fungal, or viral antigen, or a combination thereof. The antigen can take the form of an inactivated whole or partial cell or virus preparation, or the form of antigenic molecules obtained by conventional protein purification, genetic engineering techniques or chemical synthesis.

In a further embodiment, the present invention provides methods of preparing vaccine compositions containing an antigen or antigens combined with a submicron oil-in-water emulsion.

In preparing the vaccine compositions of the present invention, the antigen(s) can be combined either intrinsically (e.g., prior to microfluidization) or extrinsically (e.g., after microfluidization) with the components of the oil-in-water emulsion. Preferably, the antigen is combined with the components of the oil-in-water emulsion intrinsically.

In still another embodiment, the present invention provides vaccine compositions which contain a microencapsulated antigen and a submicron oil-in-water emulsion described hereinabove, where the microencapsulated antigen is combined with the emulsion extrinsically.

It has also been surprisingly discovered that a saponin and a sterol, when combined in solution, associate with each other to form complexes in the form of helical micelles. According to the present invention, these helical micelle complexes have immunostimulating activities and are especially useful as adjuvants in vaccine compositions.

Accordingly, the present invention provides vaccine compositions containing a saponin and a sterol, wherein the saponin and the sterol form complexes in the form of helical micelles. The present invention also provides compositions containing a saponin, a sterol and an antigen, wherein the saponin and the sterol form complexes in the form of helical micelles, and wherein the antigen is admixed with but not incorporated within the helical micelles.

DETAILED DESCRIPTION OF THE INVENTION

Figure 1:
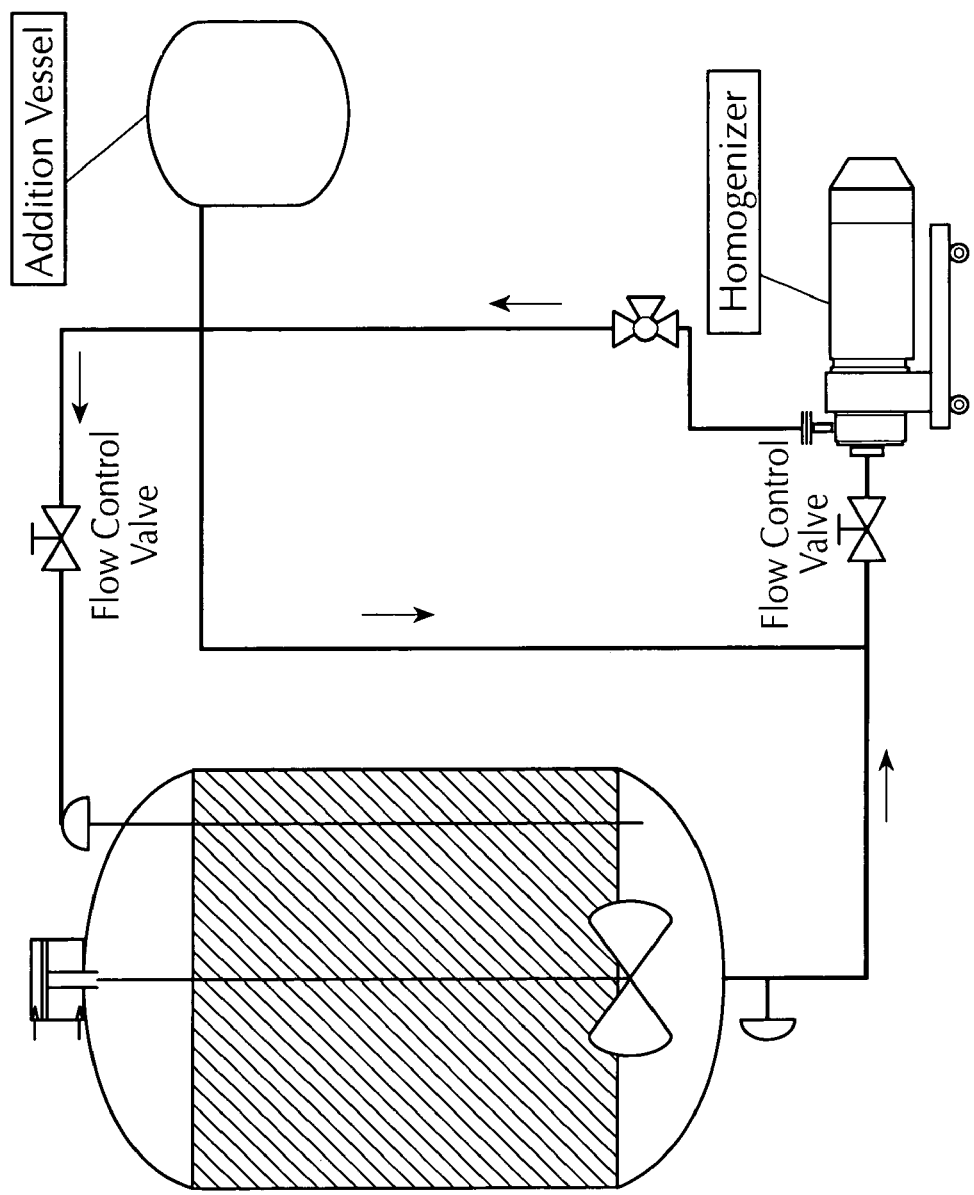
FIG. 1 depicts the process for the batch preparation of non-microfluidized vaccine compositions. In this process the various vaccine components are added to the addition vessel on the left and ultimately pumped into the blend vessel where the components are mixed together through simple mechanical means.

It has been unexpectedly discovered by the present inventors that microfluidization of vaccine formulations adjuvanted with an oil-in-water emulsion comprised of a mixture of lecithin and mineral oil not only improves the physical appearance of the vaccine formulations, but also enhances the immunizing effects of the vaccine formulations. Microfluidized vaccine formulations are also characterized by an improved safety profile.

Based on these discoveries, the present invention provides submicron oil-in-water emulsions useful as an adjuvant in vaccine compositions. Methods of making these submicron oil-in-water emulsions by using a microfluidizer are also provided. Furthermore, the present invention provides submicron vaccine compositions in which an antigen is combined with a submicron oil-in-water emulsion. Methods for making such vaccine compositions are also provided. The present invention further provides vaccine compositions containing microencapsulated antigens combined with a submicron oil-in-water emulsion and methods for making such vaccines.

For clarity of disclosure, and not by way of limitation, the detailed description of the invention is divided into the following subsections which describe or illustrate certain features, embodiments or applications of the invention.

Submicron Oil-in-Water Emulsions

In one embodiment, the present invention provides submicron oil-in-water emulsion formulations useful as a vaccine adjuvant. The submicron oil-in-water emulsions of the present invention enhance the immunogenicity of antigens in vaccine compositions, are safe for administration to animals and stable during storage.

The submicron oil-in-water emulsions of the present invention are composed of a non-metabolizable oil, at least one surfactant, and an aqueous component, where the oil is dispersed in the aqueous component with an average oil droplet size in the submicron range.

By "submicron" is meant that the droplets are of a size of less than 1 µm (micron) and the average or mean oil droplet size is less than 1 µm. Preferably, the mean droplet size of the emulsion is less than 0.8 µm; more preferably, less than 0.5 µm; and even more preferably, less than 0.4 µm, or about 0.1–0.3 µm.

The "mean droplet size" is defined as the Volume Mean Diameter (VMD) particle size within a volume distribution of particle sizes. The VMD is calculated by multiplying each particle diameter by the volume of all particles of that size and summing. This is then divided by the total volume of all particles.

The term "non-metabolizable oil" as used herein refers to oils that cannot be metabolized by the body of the animal subject to which the emulsion is administered.

The terms "animal" and "animal subject" as used herein refer to all non-human animals, including cattle, sheep, and pigs, for example.

Non-metabolizable oils suitable for use in the emulsions of the present invention include alkanes, alkenes, alkynes, and their corresponding acids and alcohols, the ethers and esters thereof, and mixtures thereof. Preferably, the individual compounds of the oil are light hydrocarbon compounds, i.e., such components have 6 to 30 carbon atoms. The oil can be synthetically prepared or purified from petroleum products. Preferred non-metabolizable oils for use in the emulsions of the present invention include mineral oil, paraffin oil, and cycloparaffins, for example.

The term "mineral oil" refers to a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, 18$^{th}$ Edition (Easton, Pa.: Mack Publishing Company, 1990, at pages 788 and 1323). Mineral oil can be obtained from various commercial sources, for example, J.T. Baker (Phillipsburg, Pa.), USB Corporation (Cleveland, Ohio). Preferred mineral oil is light mineral oil commercially available under the name DRAKEOL®.

Typically, the oil component of the submicron emulsions of the present invention is present in an amount from 1% to 50% by volume; preferably, in an amount of 10% to 45; more preferably, in an amount from 20% to 40%.

The oil-in-water emulsions of the present invention typically include at least one (i.e., one or more) surfactant. Surfactants and emulsifiers, which terms are used interchangeably herein, are agents which stabilize the surface of the oil droplets and maintain the oil droplets within the desired size.

Surfactants suitable for use in the present emulsions include natural biologically compatible surfactants and non-natural synthetic surfactants. Biologically compatible surfactants include phospholipid compounds or a mixture of phospholipids. Preferred phospholipids are phosphatidylcholines (lecithin), such as soy or egg lecithin. Lecithin can be obtained as a mixture of phosphatides and triglycerides by water-washing crude vegetable oils, and separating and drying the resulting hydrated gums. A refined product can be obtained by fractionating the mixture for acetone insoluble phospholipids and glycolipids remaining after removal of the triglycerides and vegetable oil by acetone washing. Alternatively, lecithin can be obtained from various commercial sources. Other suitable phospholipids include phosphatidylglycerol, phosphatidylinositol, phosphatidylserine, phosphatidic acid, cardiolipin, and phosphatidylethanolamine. The phospholipids may be isolated from natural sources or conventionally synthesized.

Non-natural, synthetic surfactants suitable for use in the submicron emulsions of the present invention include sorbitan-based non-ionic surfactants, e.g. fatty-acid-substituted sorbitan surfactants (commercially available under the name SPAN® or ARLACEL®), fatty acid esters of polyethoxylated sorbitol (TWEEN®), polyethylene glycol esters of fatty acids from sources such as castor oil (EMULFOR); polyethoxylated fatty acid (e.g., stearic acid available under the name SIMULSOL M-53), polyethoxylated isooctylphenol/formaldehyde polymer (TYLOXAPOL), polyoxyethylene fatty alcohol ethers (BRIJ®); polyoxyethylene nonphenyl ethers (TRITON® N), polyoxyethylene isooctylphenyl ethers (TRITON® X). Preferred synthetic surfactants are the surfactants available under the name SPAN® and TWEEN®.

Preferred surfactants for use in the oil-in-water emulsions of the present invention include lecithin, Tween-80 and SPAN-80.

Generally speaking, the surfactant, or the combination of surfactants, if two or more surfactants are used, is present in the emulsion in an amount of 0.01% to 10% by volume, preferably, 0.1% to 6.0%, more preferably 0.2% to 5.0%.

The aqueous component constitutes the continuous phase of the emulsion and can be water, buffered-saline or any other suitable aqueous solution.

The oil-in-water emulsions of the present invention can include additional components that are appropriate and desirable, including preservatives, osmotic agents, bioadhesive molecules, and immunostimulatory molecules.

It is believed that bioadhesive molecules can enhance the delivery and attachment of antigens on or through the target mucous surface conferring mucosal immunity. Examples of suitable bioadhesive molecules include acidic non-naturally occurring polymers such as polyacrylic acid and polymethacrylic acid (e.g., CARBOPOL®, CARBOMER); acidic synthetically modified natural polymers such as carboxymethylcellulose; neutral synthetically modified natural polymers such as (hydroxypropyl) methylcellulose; basic amine-bearing polymers such as chitosan; acidic polymers obtainable from natural sources such as alginic acid, hyaluronic acid, pectin, gum tragacanth, and karaya gum; and neutral non-naturally occurring polymers, such as polyvinylalcohol; or combinations thereof.

The phrase "immunostimulatory molecules", as used herein, refers to those molecules that enhance the protective immune response induced by an antigenic component in vaccine compositions. Suitable immunostimulatory materials include bacterial cell wall components, e.g., derivatives of N-acetyl muramyl-L-alanyl-D-isoglutamine such as murabutide, threonyl-MDP and muramyl tripeptide; saponin glycosides and derivatives thereof, e.g., Quil A, QS 21 and GPI-0100; cholesterol; and quaternary ammonium compounds, e.g., dimethyldioctadecylammonium bromide (DDA) and N,N-dioctadecyl-N,N-bis(2-hydroxyethyl)propanediamine ("avridine").

Saponis are glycosidic compounds that are produced as secondary metabolites in a wide variety of plant species. The chemical structure of saponins imparts a wide range of pharmacological and biological activities, including some potent and efficacious immunological activity.

Structurally, saponins consist of any aglycone attached to one or more sugar chains. Saponins can be classified according to their aglycone composition: Triterpene glycosides, Steroid glycosides, and Steroid alkaloid glycosides.

Saponin can be isolated from the bark of *Quillaja saponaria*. Saponin has long been known as an immunostimulator. Dalsgaard, K., "Evaluation of its adjuvant activity with a special reference to the application in the vaccination of cattle against foot-and-mouth disease", *Acta. Vet. Scand.* 69: 1–40 1978. Crude extracts of plants containing saponin enhanced potency of foot and mouth disease vaccines. However, the crude extracts were associated with adverse side effects when used in vaccines. Subsequently, Dalsgaard partially purified the adjuvant active component from saponin by dialysis, ion exchange and gel filtration chromatography. Dalsgaard, K. et al., "Saponin adjuvants III. Isolation of a substance from *Quillaja saponaria* Morina with adjuvant activity in foot-and-mouth disease vaccines", *Arch. Gesamte. Virusforsch.* 44: 243–254 1974. An adjuvant active component purified in this way is known as "Quil A." On a weight basis Quil A showed increased potency and exhibited reduced local reactions when compared to crude saponin. Quil A is widely used in veterinary vaccines.

Further analysis of Quil A by high pressure liquid chromatography (HPLC) revealed a heterogenous mixture of closely related saponins and led to discovery of QS21 which was a potent adjuvant with reduced or minimal toxicity. Kensil C. R. et al., "Separation and characterization of saponins with adjuvant activity from *Quillaja saponaria* Molina cortex," *J. Immunol.* 146: 431–437, 1991. Unlike most other immunostimulators, QS 21 is water-soluble and can be used in vaccines with or without emulsion type formulations. QS21 has been shown to elicit a Th1 type response in mice stimulating the production of IgG2a and IgG2b antibodies and induced antigen-specific CD8+ CTL (MHC class 1) in response to subunit antigens. Clinical studies in humans have proved its adjuvanticity with an acceptable toxicological profile. Kensil, C. R. et al., "Structural and imunological charaterization of the vaccine adjuvant QS-21. In Vaccine Design: the subunit and Adjvuant Approach," Eds. Powell, M. F. and Newman, M.J. Plenum Publishing Corporation, New York. 1995, pp. 525–541.

U.S. Pat. No. 6,080,725 teaches the methods of making and using saponin-lilpophile conjugate. In this saponin-lipophile conjugate, a lipophile moiety such as lipid, fatty acid, polyethylene glycol or terpene is covalently attached to a non-acylated or desacylated triterpene saponin via a carboxy group present on the 3-O-glucuronic acid of the triterpene saponin. The attachment of a lipophilic moiety to the 3-O-glucuronic acid of a saponin such as *Quillaja desacylsaponin, lucyoside* P, or saponin from *Gypsophila, saponaria* and *Acanthophyllum* enhances their adjuvant effects on humoral and cell-mediated immunity. Additionally, the attachment of a lipophile moiety to the 3-O-glucuronic acid residue of non- or desacylsaponin yields a saponin analog that is easier to purify, less toxic, chemically more stable, and possesses equal or better adjuvant properties than the original saponin.

GPI-0100 is a saponin-lipophile conjugate described in the U.S. Pat. No. 6,080,725. GPI-0100 is produced by the addition of aliphatic amine to desacylsaponin via the carboxyl group of glucuronic acid.

Quaternary ammonium compounds—A number of aliphatic nitrogenous bases have been proposed for use as immunological adjuvants, including amines, quaternary ammonium compounds, guanidines, benzamidines and thiouroniums. Specific such compounds include dimethyldioctadecylammonium bromide (DDA) and N,N-dioctadecyl-N,N-bis(2-hydroxyethyl)propanediamine ("avridine").

U.S. Pat. No. 5,951,988 teaches adjuvant formulation containing quarternary ammonium salts such as DDA in conjunction with an oil component. This formulation is useful in conjunction with known immunological substances, e.g., viral or bacterial antigens in a vaccine composition, in order to enhance the immunogenic response. The composition is also useful without an incorporated antigen as nonspecific immunostimulatory formulation.

U.S. Pat. No. 4,310,550 describes the use of N,N-higher alkyl-N',N'-bis(2-hydroxyethyl)-propanediamine and N,N-higher alkyl-xylylenediamines formulated with fat or lipid emulsion as a vaccine adjuvant. A method of inducing or enhancing the immunogenic response of an antigen in man or an animal through parenteral administration of the adjuvant formulation is described in the U.S. Pat. No. 4,310,550.

In a preferred embodiment, the present invention provides a submicron oil-in-water emulsion useful as vaccine adjuvant, which is composed of an AMPHIGEN® formulation, with droplets of a size less than 1 μm and a mean droplet size of about 0.25 μm.

The term "AMPHIGEN® formulation" as used herein refers to a solution formed by mixing a DRAKEOL® lecithin oil solution (Hydronics, Lincoln, Nebr.) with saline solution in the presence of TWEEN® 80 and SPAN® 80. A typical AMPHIGEN® formulation contains 40% light mineral oil by volume (v/v), about 25% w/v lecithin, about 0.18% TWEEN 80 by volume (v/v) and about 0.08% Span 80 by volume (v/v).

Methods of Preparing Submicron Oil-in-Water Emulsions

In another embodiment, the present invention provides methods of preparing the suomicron oil-in-water emulsions described hereinabove.

According to the present invention, the various components of the emulsion, including oil, one or more surfactants, an aqueous component and any other component appropriate for use in the emulsion, are combined and mixed together.

The mixture formed is subjected to an emulsification process, typically by passage one or more times through one or more homogenizers or emulsifiers to form an oil-in-water emulsion which has a uniform appearance and an average droplet size of about 0.5 μm. Any commercially available homogenizer or emulsifier can be used for this purpose, e.g., Ross emulsifier (Hauppauge, N.Y.), Gaulin homogenizer (Everett, Mass.).

The emulsion so formed is then subjected to microfluidization to bring the droplet size in the submicron range. Microfluidization can be achieved by use of a commercial mirofluidizer, such as model number 11OY available from Microfluidics, Newton, Mass.; Gaulin Model 30CD (Gaulin, Inc., Everett, Mass.); and Rainnie Minilab Type 8.30H (Miro Atomizer Food and Dairy, Inc., Hudson, Wis.). These microfluidizers operate by forcing fluids through small apertures under high pressure, such that two fluid streams interact at high velocities in an interaction chamber to form emulsions with droplets of a submicron size.

Droplet size can be determined by a variety of methods known in the art, e.g., laser diffraction, by use of commercially available sizing instruments. The size may vary depending on the type of surfactant used, the ratio of surfactant to oil, operating pressure, temperature, and the like. The skilled artisan can determine the desired combination of these parameters to obtain emulsions with desired droplet size without undue experimentation. The droplets of the emulsions of the present invention are less than 1 μm in diameter, preferably with a mean droplet size of less than 0.8 μm, and more preferably with a mean droplet size less than 0.5 μm, and even more preferably with a mean droplet size of less than 0.3 μm.

In a preferred embodiment of the present invention, the DRAKEOL lecithin oil solution, which is commercially available from Hydronics (Lincoln, Nebr.) and contains 25% lecithin in light mineral oil, is combined and mixed with saline as well as surfactants TWEEN® 80 and SPAN® 80 to form an "AMPHGEN® solution" or "AMPHIGEN® formulation". The AMPHIGEN® solution is then emulsified with a Ross® (Hauppauge, N.Y. 11788) emulsifier at approximately 3400 rpm to form an oil-in-water emulsion. Subsequently the emulsion is passed once through a Microfluidizer operating at about 4500±500 psi. The microfluidized oil-in-water emulsion has droplets of a size less than 1 μm, with a mean droplet size of about 0.25 μm.

Vaccine Compositions Containing Antigens Incorporated in Submicron Oil-in-Water Emulsions In another embodiment, the present invention provides vaccine compositions which contain an antigen(s) and a submicron oil-in-water emulsion described hereinabove. These vaccine compositions are characterized by having an enhanced immunogenic effect and an improved physical appearance (e.g., no phase separation is observed after an extended period of storage). In addition, the vaccine compositions of the present invention are safe for administration to animals.

According to the present invention, the antigen can be combined with the emulsion extrinsically, or preferably, intrinsically. The term "intrinsically" refers to the process wherein the antigen is combined with the emulsion components prior to the microfluidization step. The term "extrinsically" refers to the process where the antigen is added to the emulsion after the emulsion has been microfluidized. The extrinsically added antigen can be free antigen or it can be encapsulated in microparticles as further described herein below.

The term "antigen" as used herein refers to any molecule, compound or composition that is immunogenic in an animal and is included in the vaccine composition to elicit a protective immune response in the animal to which the vaccine composition is administered.

The term "immunogenic" as used in connection with an antigen refers to the capacity of the antigen to provoke an immune response in an animal against the antigen. The immune response can be a cellular immune response mediated primarily by cytotoxic T-cells, or a humoral immune response mediated primarily by helper T-cells, which in turn activates B-cells leading to antibody production.

A "protective immune response" is defined as any immune response, either antibody or cell mediated immune response, or both, occurring in the animal that either prevents or detectably reduces the occurrence, or eliminates or detectably reduces the severity, or detectably slows the rate of progression, of the disorder or disease caused by the antigen or a pathogen containing the antigen.

Antigens which can be included in the vaccine composition of the present invention include antigens prepared from pathogenic bacteria such as *Mycoplasma hyopneumoniae*, *Haemophilus somnus*, *Haemophilus parasuis*, *Bordetella*

*bronchiseptica, Actinobacillus pleuropneumonie, Pasteurella multocida, Manheimia hemolytica, Mycoplasma bovis, Mycoplasma galanacieum, Mycobacterium bovis, Mycobacterium paratuberculosis, Clostridial* spp., *Streptococcus uberis, Streptococcus suis, Staphylococcus aureus, Erysipelothrix rhusopathiae, Campylobacter* spp., *Fusobacterium necrophorum, Escherichia coli, Salmonella enterica serovars, Leptospira*spp.; pathogenic fungi such as *Candida*; protozoa such as *Cryptosporidium parvum, Neospora canium, Toxoplasma gondii, Eimeria* spp.; helminths such as *Ostertagia, Cooperia, Haemonchus, Fasciola*, either in the form of an inactivated whole or partial cell preparation, or in the form of antigenic molecules obtained by conventional protein purification, genetic engineering techniques or chemical synthesis. Additional antigens include pathogenic viruses such as Bovine herpesviruses-1,3,6, Bovine viral diarrhea virus (BVDV) types 1 and 2, Bovine parainfluenza virus, Bovine respiratory syncytial virus, bovine leukosis virus, rinderpest virus, foot and mouth disease virus, rabies, swine fever virus, African swine fever virus, Porcine parvovirus, PRRS virus, Porcine circovirus, influenza virus, swine vesicular disease virus, Techen fever virus, Pseudorabies virus, either in the form of an inactivated whole or partial virus preparation, or in the form of antigenic molecules obtained by conventional protein purification, genetic engineering techniques or chemical synthesis.

The amount of the antigen should be such that the antigen which, in combination with the oil-in-water emulsion, is effective to induce a protective immune response in an animal. The precise amount of an antigen to be effective depends on the nature, activity and purity of the antigen, and can be determined by one skilled in the art.

The amount of the oil-in-water emulsion present in the vaccine compositions should be sufficient for potentiating the immunogenicity of the antigen(s) in the vaccine compositions. When desirable and appropriate, additional amounts of surfactant(s) or additional surfactant(s) can be added in the vaccine composition in addition to the surfactant(s) provided by the oil-in-water emulsion. Generally speaking, the oil component is present in the final volume of a vaccine composition in an amount from 1.0% to 20% by volume; preferably, in an amount of 1.0% to 10%; more preferably, in an amount from 2.0% to 5.0%. The surfactant, or the combination of surfactants if two or more surfactants are used, is present in the final volume of a vaccine composition in an amount of 0.1% to 20% by volume, preferably, 0.15% to 10%, more preferably 0.2% to 6.0%.

In addition to the antigen(s) and the oil-in-water emulsion, the vaccine composition can include other components which are appropriate and desirable, such as preservatives, osmotic agents, bioadhesive molecules, and immunostimulatory molecules (e.g., Quil A, cholesterol, GPI-0100, dimethyldioctadecylammonium bromide (DDA)), as described hereinabove in connection with the oil-in-water emulsion.

The vaccine compositions of the present invention can also include a veterinarily-acceptable carrier. The term "a veterinarily-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others.

In a preferred embodiment, the present invention provides a vaccine composition which includes at least one of a BVDV type I or BVDV type II antigen, incorporated intrinsically in an oil-in-water emulsion which has droplets of a size of less than 1 μm, preferably with a mean droplet size of less than 0.8 μm, more preferably less than 0.5 μm, and even more preferably with a mean droplet size of about 0.5 μm. The BVDV type I and/or II antigen is preferably in the form of an inactivated viral preparation. The submicron oil-in-water emulsion preferably is composed of an AMPHIGEN® formulation (i.e., a formulation which contains light mineral oil, lecithin, TWEEN® 80, and SPAN® 80). The vaccine composition preferably also includes Quil-A, cholesterol, and thimerosol.

In another preferred embodiment, the present invention provides a vaccine composition which includes a Leptospira antigen and at least one of a BVDV type I or BVDV type II antigen in an oil-in-water emulsion. The antigens, preferably in the form of inactivated cell or viral preparation, are incorporated intrinsically in the oil-in-water emulsion having droplets of a size of less than 1 μm, preferably with a mean droplet size of less than 0.8 μm, more preferably less than 0.5 μm, and even more preferably with a mean droplet size of about 0.5 μm. The submicron oil-in-water emulsion preferably is composed of an AMPHIGEN formulation (i.e., a formulation which contains light mineral oil, lecithin, TWEEN® 80, and SPAN® 80). The vaccine composition preferably also includes one or more immunostimulatory molecules selected from Quil-A, cholesterol, DDA, GPI-100 and aluminum hydroxide (AIOH).

In still another preferred embodiment, the present invention provides a vaccine composition which includes at least one bacterial antigen, e.g., the recombinant *Streptococcus uberis* PauA protein or a cell preparation of *E. coli* or a combination of both, in an oil-in-water emulsion. The antigen(s) is combined intrinsically with the oil-in-water emulsion which has droplets of a size of less than 1 μm, preferably with a mean droplet size of less than 0.8 μm, more preferably less than 0.5 μm, and even more preferably with a mean droplet size of about 0.25 μm. The submicron oil-in-water emulsion preferably is composed of an AMPHIGEN(® formulation (i.e., a formulation which contains light mineral oil, lecithin, TWEEN(® 80, and SPAN® 80). The vaccine composition preferably also includes one or more immunostimulatory molecules selected from Quil A, DDA and GPI-100.

The vaccine compositions of the present invention can be administered to an animal by known routes, including the oral, intranasal, mucosal, topical, transdermal, and parenteral (e.g., intravenous, intraperitoneal, intradermal, subcutaneous or intramuscular) route. Administration can be achieved using a combination of routes, e.g., first administration using a parental route and subsequent administration using a mucosal route.

Methods of Preparing Vaccine Compositions

In a further embodiment, the present invention provides methods of preparing vaccine compositions containing an antigen or antigens and a submicron oil-in-water emulsion.

In preparing the vaccine compositions of the present invention, the antigen(s) can be combined either intrinsically or extrinsically with the components of the oil-in-water emulsion. Preferably, the antigen is combined with the components of the oil-in-water emulsion intrinsically.

The antigen can be combined with the various components of the emulsion, including oil, one or more surfactants, an aqueous component and any other appropriate component, to form a mixture. The mixture is subjected to a primary blending process, typically by passage one or more times through one or more homogenizers or emulsifiers, to form an oil-in-water emulsion containing the antigen. Any commercially available homogenizer or emulsifier can be used for this purpose, e.g., Ross emulsifier (Hauppauge, N.Y.), Gaulin homogenizer (Everett, Mass.), or Microfluidics (Newton, Mass.). Alternatively, the various components of the emulsion adjuvant, including oil, one or more surfactants, and an aqueous component can be combined first to form an oil-in-water emulsion by using a homogenizer or emulsifier; and the antigen is then added to this emulsion. The mean droplet size of the oil-in-water emulsion after the primary blending is approximately 1.0–1.2 micron.

The emulsion containing the antigen is then subjected to microfluidization to bring the droplet size in the submicron range. Microfluidization can be achieved by use of a commercial mirofluidizer, such as model number 11OY available from Microfluidics, Newton, Mass.; Gaulin Model 30CD (Gaulin, Inc., Everett, Mass.); and Rainnie Minilab Type 8.30H (Miro Atomizer Food and Dairy, Inc., Hudson, Wis.).

Droplet size can be determined by a variety of methods known in the art, e.g., laser diffraction, by use of commercially available sizing instruments. The size may vary depending on the type of surfactant used, the ratio of surfactant to oil, operating pressure, temperature, and the like. One can determine a desired combination of these parameters to obtain emulsions with a desired droplet size. The oil droplets of the emulsions of the present invention are less than 1 µm in diameter. Preferably the mean droplet size is less than 0.8 µm. More preferably, the mean droplet size is less than 0.5 µm. Even more preferably, the mean droplet size is about 0.1 to 0.3 µm.

In a preferred embodiment of the present invention, the DRAKEOL® lecithin oil solution, which contains 25% lecithin in light mineral oil, is combined and mixed with surfactants TWEEN® 80 and SPAN® 80 and saline solution to form a mixture that contains 40% light mineral oil, lecithin, 0.18% TWEEN® 80, and 0.08% SPAN® 80. The mixture is then emulsified with a Ross® (Hauppauge, N.Y. 11788) emulsifier at approximately 3400 rpm to form an emulsion product, which is also referred to as an "AMPHIGEN® formulation" or "AMPHIGEN® solution". Subsequently, the desired antigen(s) are combined with the AMPHIGEN® solution and any other appropriate components (e.g., immunostimulatory molecules) with the aid of an emulsifier, e.g., a Ross homogenizer, to form an oil-in-water emulsion containing the antigen(s). Such emulsion is passed once through a Microfluidizer operating at about 10000±500 psi. The microfluidized oil-in-water emulsion has droplets of a size of less than 1 µm, with the mean droplet size of about 0.25 µm.

In another preferred embodiment, prior to combining an oil-in-water emulsion (e.g., an AMPHIGEN® formulation) with a desired antigen(s), the antigen(s) is combined with a saponin glycoside, e.g., Quil A, to form a mixture. This antigen(s)-saponin mixture is subjected to homogenization, e.g., in a homogenization vessel. A sterol, e.g., cholesterol, is then added to the homogenized antigen(s)-saponin mixture. The mixture containing the antigen(s), saponin and sterol is then subjected to further homogenization. The homogenized antigen(s)-saponin-sterol mixture is then combined with an oil-in-water emulsion (e.g., an AMPHIGEN® formulation) with the aid of a homogenizer, for example. The homogenized oil-in-water emulsion containing the antigen(s), saponin and sterol is then subjected to high pressure homogenization, such as microfluidization.

Vaccine Compositions Containing Microencapsulated Antigens in a Submicron Oil-in-Water Emulsion and Methods of Preparation In still another embodiment, the present invention provides vaccine compositions which contain an antigen encapsulated in microparticles (or "microencapsulated antigen"), where the microencapsulated antigen is extrinsically incorporated into a submicron oil-in-water emulsion described hereinabove.

Methods for absorbing or entrapping antigens in particulate carriers are known in the art. See, e.g., Pharmaceutical Particulate Carriers: Therapeutic Applications (Justin Hanes, Masatoshi Chiba and Robert Langer. Polymer microspheres for vaccine delivery. In: Vaccine design. The subunit and adjuvant approach. Eds. Michael F. Powell and Mark J. Newman, 1995 Plenum Press, New York and London ). Particulate carriers can present multiple copies of a selected antigen to the immune system in an animal subject and promote trapping and retention of antigens in local lymph nodes. The particles can be phagocytosed by macrophages and can enhance antigen presentation through cytokine release. Particulate carriers have also been described in the art and include, e.g., those derived from polymethyl methacrylate polymers, as well as those derived from poly (lactides) and poly(lactide-co-glycolides), known as PLG. Polymethyl methacrylate polymers are non-biodegradable while PLG particles can be biodegrade by random non-enzymatic hydrolysis of ester bonds to lactic and glycolic acids which are excreted along normal metabolic pathways.

Biodegradable microspheres have also used to achieve controlled release of vaccines. For example, a continuous release of antigen over a prolonged period can be achieved. Depending upon the molecular weight of the polymer and the ratio of lactic to glycolic acid in the polymer, a PLGA polymer can have a hydrolysis rate from a few days or weeks to several months or a year. A slow, controlled release may result in the formation of high levels of antibodies similar to those observed after multiple injections. Alternatively, a pulsatile release of vaccine antigens can be achieved by selecting polymers with different rates of hydrolysis. The rate of hydrolysis of a polymer typically depends upon the molecular weight of the polymer and the ratio of lactic to glycolic acid in the polymer. Microparticles made from two or more different polymers with varying rates of antigen release provide pulsatile releases of antigens and mimics multiple-dose regimes of vaccination.

According to the present invention, an antigen, including any of those described hereinabove, can be absorbed to a particulate polymer carrier, preferably a PLG polymer, by using any procedure known in the art (such as one exemplified in Example 17), to form a microencapsulated antigen preparation. The microencapsulated antigen preparation is then mixed with and dispersed in a submicron oil-in-water emulsion, which emulsion has been described hereinabove, to form the vaccine composition.

In a preferred embodiment, the present invention provides a vaccine composition which contains an antigen encapsulated in a PLG polymer, wherein the microencapsulated antigen is dispersed extrinsically in a microfluidized oil-in-water emulsion which is composed of light mineral oil, lecithin, TWEEN80, SPAN80 and saline, and has a mean droplet size of less than 1.0 µm.

Complexes Formed by a Saponin and Sterol

In one embodiment, the present invention provides compositions containing a saponin and a sterol, wherein the saponin and the sterol form complexes in the form of helical micelles. According to the present invention, these complexes have immunostimulating activities.

By "immunostimulating" is meant that the complexes can enhance the immune response induced by an antigenic component, or that the complexes can induce an immune response independent of a separate antigenic component.

In accordance with the present invention, a preferred saponin for use in a composition of the present invention is Quil A.

Preferred sterols for use in the adjuvant compositions of the present invention include beta-sitosterol, stigmasterol, ergosterol, ergocalciferol and cholesterol. These sterols are well known in the art, for example cholesterol is disclosed in the Merck Index, 11th Edn., page 341, as a naturally occurring sterol found in animal fat. Most preferably the sterol is cholesterol.

The ratio of saponin:sterol in the composition is typically on the order of 1:100 to 5:1 weight to weight. Preferably, the ratio is 1:1.

In another embodiment, the present invention provides vaccine compositions containing a saponin, a sterol and an antigen, wherein the saponin and the sterol form complexes in the form of helical micelles, and wherein the antigen is admixed with but not incorporated within the helical micelles.

Below are examples of specific embodiments for carrying out the present invention. The examples are offered for illustrative purposes only, and are not intended to limit the scope of the present invention in any way.

EXAMPLE 1

Preparation of an AMPHIGEN® Formulation

An AMPHIGEN® formulation was prepared in a two-step process. In the first step, 80 liters of Drakeol Lecithin oil solution, 116 liters of Tetanus Toxoid saline, 1.2 liters of SPAN 80, and 2.8 liters of Tween 80 were mixed together and emulsified using a Ross emulsifier. The Drakeol Lecithin oil solution contained 25% soya lecithin and 75% mineral oil. Emulsified product was recirculated through Ross emulsifier for a minimum of 5 volumes or a minimum of 10 minutes. The emulsified product was stored at 2–7° C. for a maximum of 24 hours for further processing. The emulsion from the Ross emulsifier tank was transferred to a Gaulin homogenizer and was homogenized for 20 minutes under a pressure of 4500 psi. The resulting 40% Drakeol Lecithin oil solution (hereinafter the "AMPHIGEN® formulation" or "AMPHIGEN® solution") was then dispensed into sterile polypropylene carboxy containers. The dispensing was performed inside a class 100 dispensing hood located in a class 10,000 controlled environment. The containers were stored at 2–7° C. This AMPHIGEN® formulation was used in the experiments described hereinbelow unless indicated otherwise.

EXAMPLE 2

Primary Blending by Flashblend Homogenization of the BVD Vaccine

The apparatus used for this homogenization process is shown in FIG. 1. Using aseptic technique or steam cross valves, a bottle containing an BVD Type I antigen (an inactivated BVD Type I viral preparation) was attached to the bottom side port on the blend vessel. After the transfer of required volume of the BVD Type I antigen was completed, the BVD Type I bottle was replaced with the bottle containing an inactivated BVD Type II viral preparation (an inactivated BVD type II viral preparation). After the required amount of a BVD Type II antigen transfer was completed, the Ross homogenizer was attached to the portable vessel and the recirculation was initiated at maximum RPM (3300 rpm). Vessel agitation was maintained at medium speed.

Using aseptic technique or stream cross valve, a bottle containing Quil-A at 50 mg/ml concentration was attached to the homogenizer in-line port on the blend vessel. A required amount of the Quil-A solution was passed into the vessel through line suction. After the transfer of the Quil-A solution was completed, the bottle was removed. In the same way, a required amount of cholesterol in ethanol solution (18 mg/ml) was transferred to the blend vessel. Subsequently, a required amount of the AMPHIGEN® formulation, 10% thimerosol solution, and Basic Modified Eagles media ("BME") extender solutions were added to the blend vessel.

Once all the additions were complete, the mixing was continued for an additional 15 minutes. The resulting formulation was aliquoted into 2 ml doses and represented a non-microfluidized AMPHIGEN® formulation-based BVD vaccine. Each dose of the vaccine contained 500 μg Quil-A, 500 μg Cholesterol, 2.5% AMPHIGEN® formulation and 0.009% thimerosol. The antigen concentration for the two different BVD strains was determined in terms of the ELISA titer for gp53.

EXAMPLE 3

Secondary Blending by Microfluidization

Figure 2:
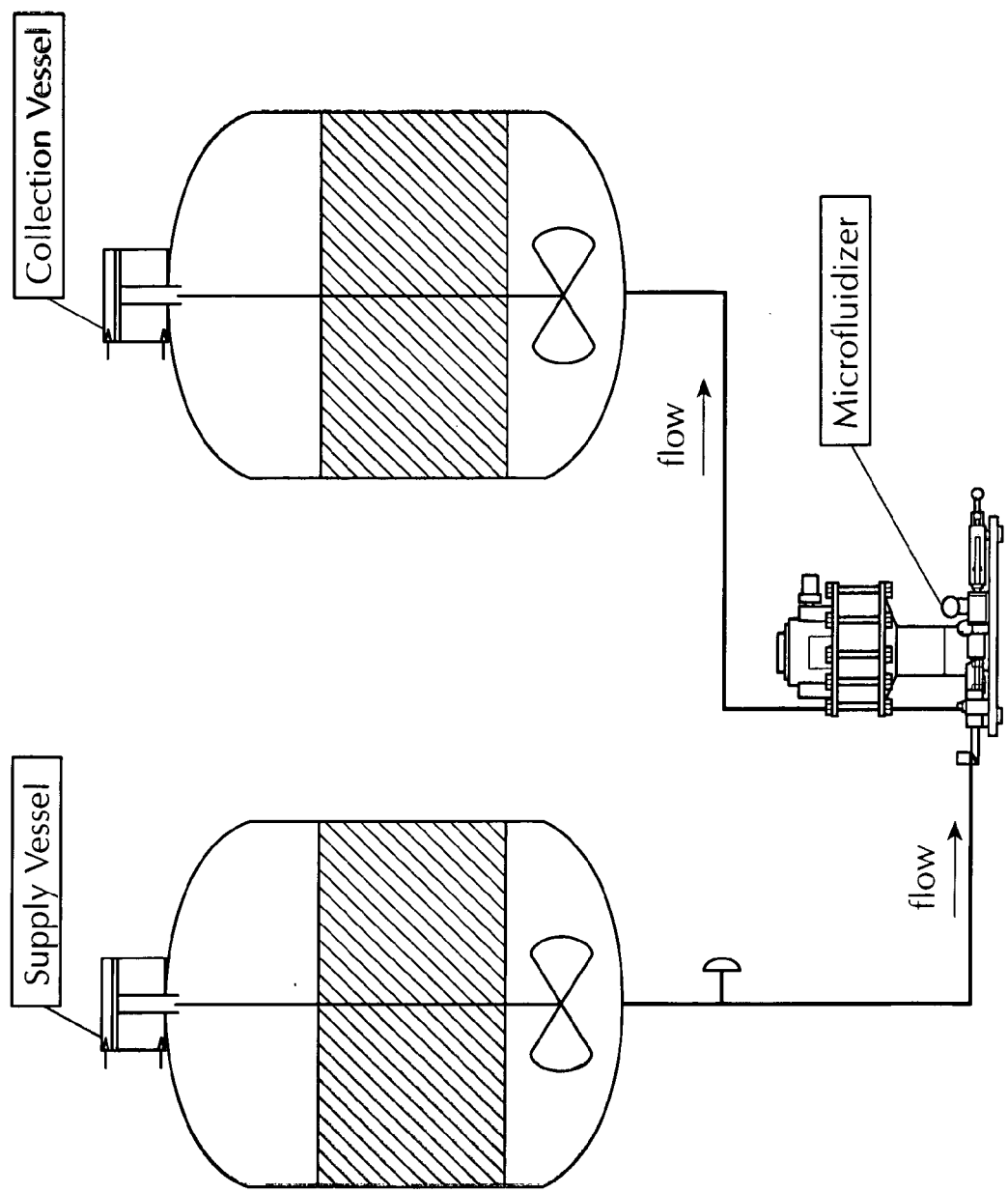
FIG. 2 depicts the process for preparation of microfluidized vaccine compositions containing intrinsically incorporated antigen. The various vaccine components are added to the addition vessel and transferred to the pre-emulsion blending unit for mixing through simple mechanical means. Subsequently, the emulsion is passed through a microfluidizer and is collected in the post-microfluidization chamber.

FIG. 2 illustrates the process used for the secondary blending through microfluidization. The microfluidizer was steam sterilized. First the auxiliary processing module chamber was installed in the unit and the blank chamber was installed on the second chamber position. The vessel containing the fully adjuvanted BVD vaccine prepared as described in the Example 2 was connected to the microfluidizer by attaching a transfer line from the supply vessel drain valve to the microfluidizer inlet. Nitrogen gas was connected to the supply vessel air filter inlet and the vessel pressure setting was adjusted to 20 +/−5 PSI. Collection vessel drain valve was connected to the transfer line from the microfluidizer outlet. After making all the necessary connections, the valves were opened and microfluidization was initiated at an operating pressure of 10,000 +/−500 PSI. The entire content of the vaccine was passed through the microfluidizer one time and was collected in the post-microfluidization chamber. This preparation was aliquoted into 2mL doses and represents the microfluidized AMPHIGEN® formulation-based BVD vaccine.

EXAMPLE 4

Preparation of a Vaccine Composition Through Bench Blend

The AMPHIGEN® formulation prepared as described in Example 1 was diluted to the 2.5% with the addition of BVD antigens and the extender. The resulting solution was blended at the bench using a stir bar instead of using a homogenizer. The final preparation contained the following composition: BVD Type 1 and Type 2 antigens, 2.5% AMPHIGEN® formulation (which contains oil, lecithin, SPAN® and TWEEN®, as described in Example 1), and saline. TWEEN 80 and SPAN 80 are present in the final vaccine preparation at 0.18% and 0.08% by volume, respectively.

EXAMPLE 5

Figure 3:
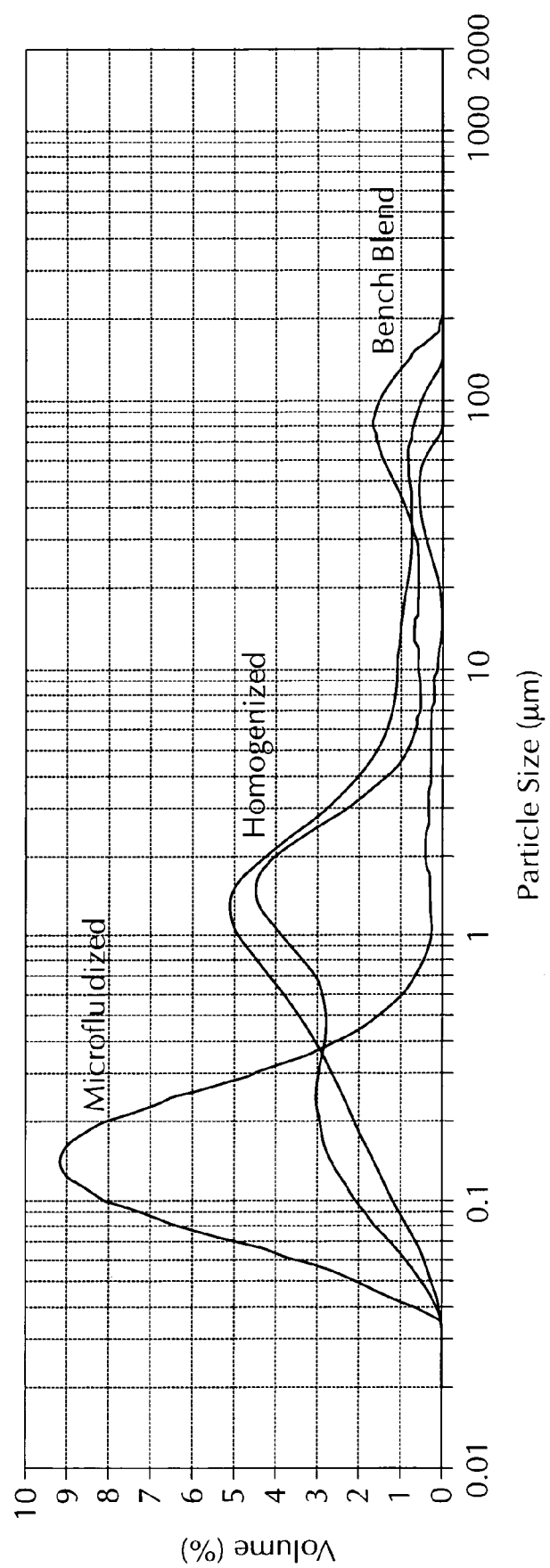
FIG. 3 depicts the droplet size distribution of the non-microfluidized AMPHIGEN® formulation-based vaccine, the microfluidized AMPHIGEN® formulation-based vaccine, and the bench blend vaccine preparation.
Figure 4:
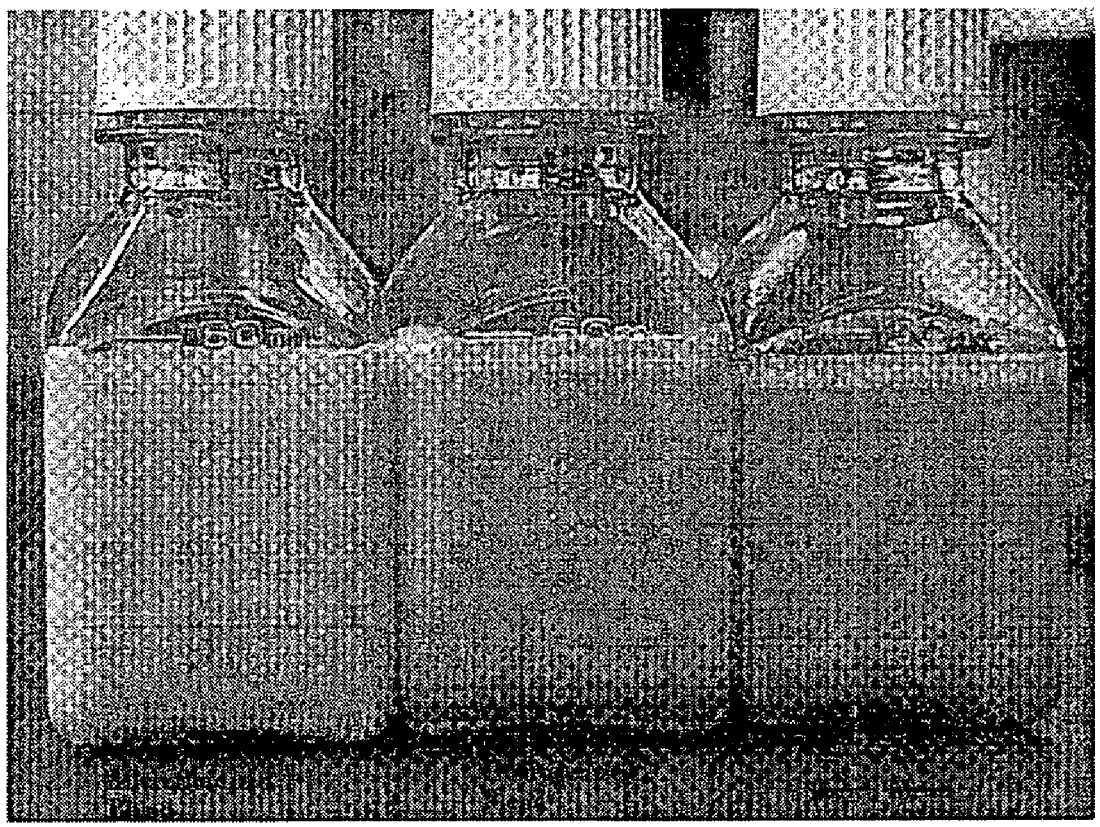
FIG. 4 shows absence of phase separation in the microfluidized vaccine preparation.
Figure 5:
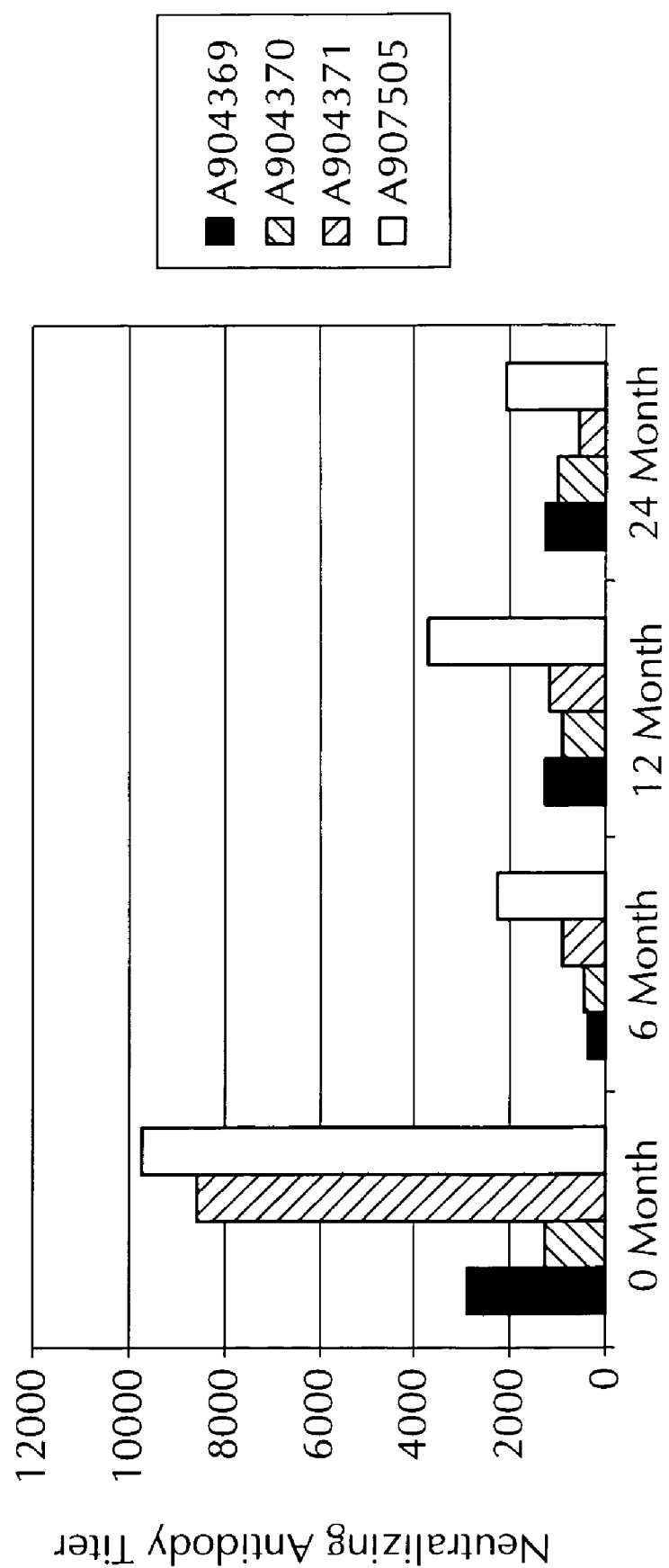
FIG. 5 depicts a comparison of the stability of antigens intrinsically incorporated in microfluidized AMPHIGEN® formulation-based vaccine preparation (A907505) and three control, non-microfluidized AMPHIGEN® formulation-based vaccine preparations (A904369, A904370, and A904371). All four vaccine preparations were stored at 4° C. for two years. At different points during the storage (0, 6, 12 or 24 months), all four formulations were used to vaccinate the three months old cows. Vaccination was done Day 0 and 21 with a 2 ml vaccine dose and the sera were collected two weeks post second vaccination. Neutralizing antibody titer for BVD Type II virus was determined in each of the serum samples. The data are presented as the geometric mean for 5 animals.
Figure 6:
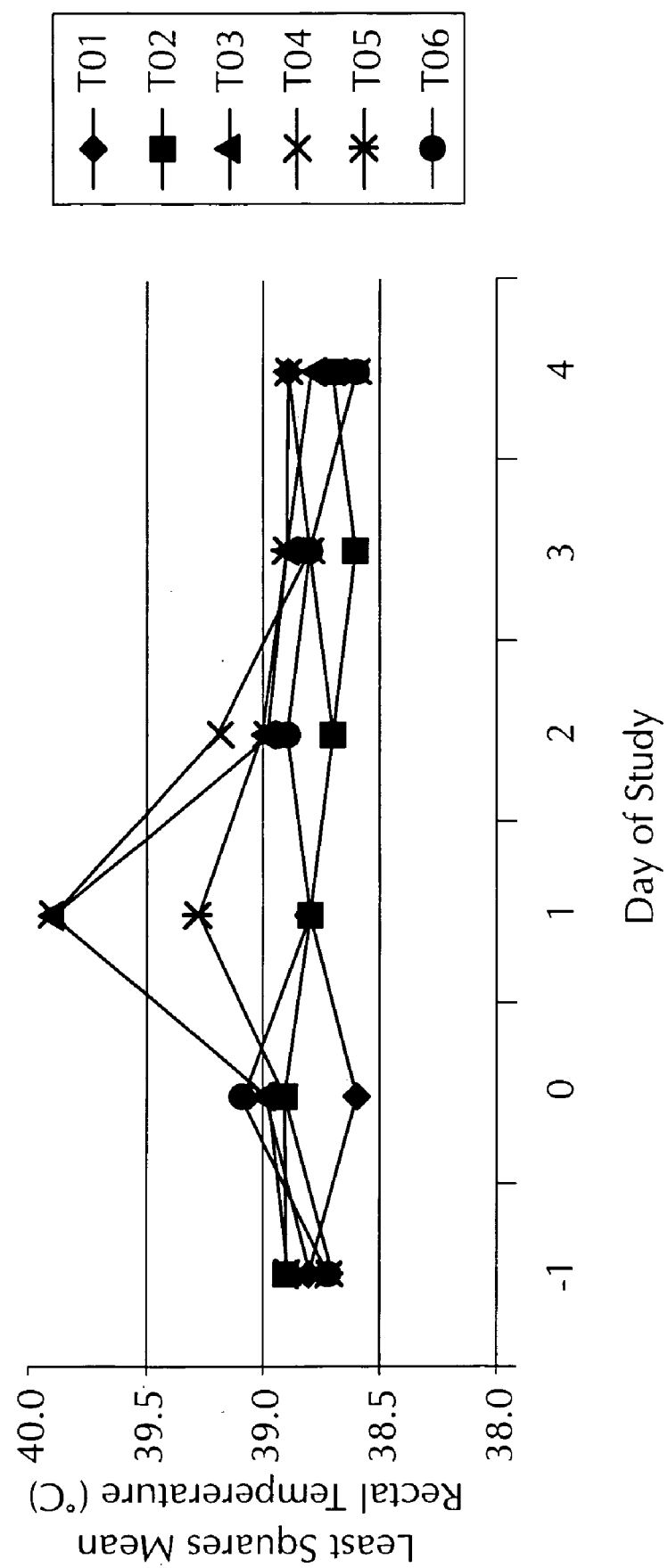
FIG. 6 shows least squares mean rectal temperature of cattle prior to and following administration of microfluidized and non-microfluidized vaccines. T01: Placebo group—single dose; T02: Placebo group—Double dose; T03: Non-microfluidized formulation—Single Dose; T04: Non-microfluidized formulation—Double dose; T05: Microfluidized formulation—Single Dose; T06: Microfluidized formulation—Double dose.

Comparison of Droplet Size Distribution between the Non-Microfluidized and Microfluidized AMPHIGEN® Formulation-Based Vaccine Preparations The non-microfluidized AMPHIGEN® formulation-based vaccine prepared as described in the Example 2, the microfluidized AMPHIGEN® formulation-based vaccine prepared as described in the Example 3, and the preparation made through bench blend as described in Example 4, were used to compare the droplet size of the vaccine preparations. Two mililiters of the sample from each of the preparations were added to a Malvern 2000 Laser Diffraction meter and the droplet size distribution was determined. As shown in FIG. 3, the results indicate that the microfluidized AMPHIGEN® formulation-based vaccine preparation had the maximum particle volume around 0.1 micron while the non-microfluidized AMPHIGEN® formulation-based vaccine preparation had the maximum particle distribution volume around 1 micron.

EXAMPLE 6

Reduction in Vaccine Phase Separation

Three different vaccine preparations: the non-microfluidized AMPHIGEN® formulation-based vaccine prepared as described in the Example 2, the microfluidized AMPHIGEN® formulation-based vaccine prepared as described in the Example 3, and the vaccine prepared through bench blend as described in Example 4, were compared side by side to determine their phase separation properties upon long storage. All these preparations were allowed to stand at 4° C. for about one month and the phase separation was monitored in terms of appearance of a creamy layer at the top of the vaccine preparations. As shown in FIG. 4, there was no phase separation in the microfluidized AMPHIGEN® formulation-based preparation when compared to the other two preparations.

EXAMPLE 7

Preparation of Microfluidized and Non-Microfluidized Cattle Vaccine against Bovine Viral Diarrhea Virus Bovine Virus Diarrhea viral antigen was intrinsically incorporated into the AMPHIGEN® formulation through microfluidization. The term "intrinsically incorporated" refers to the process whereby the antigen was added to the AMPHIGEN® formulation prior to the microfluidization. The antigen was subjected to the physical forces of the microfluidization process along with the components of the adjuvant formulation. In the control non-microfluidized group, the antigen preparation was dispersed in the AMPHIGEN® formulation through blending.

The final composition of both the control and microfluidized preparations was as follow: BVD type I with a post-inactivation ELISA titer of 2535 RU/dose for gp53, BVD Type II with a post-inactivation ELISA titer of 3290 RU/dose for gp53, Quil-A at the concentration of 1.25 mg/dose, cholesterol at the concentration of 1.25 mg/dose, the AMPHIGEN® formulation at the final concentration of 2.5%, and thimerosol at the final concentration of 0.009%. The vaccine dose was 5 ml.

EXAMPLE 8

Long term Stability of Intrinsically Incorporated BVD Viral Antigens in the Microfluidized AMPHIGEN® formulation-Based Vaccine Preparation This experiment was carried out to determine the stability of the intrinsically incorporated antigen during the long storage. Killed BVD Type II viral antigen was intrinsically incorporated into the AMPHIGEN® formulation during microfluidization process to obtain microfluidized vaccine preparation (A907505). Three other vaccine preparations containing the same antigen in non-microfluidized AMPHIGEN® formulation (A904369, A904370, and A904371) served as the control. In the non-microfluidized preparations, the antigen was mixed with AMPHIGEN® formulation and mixed through blending using a Ross homogenizer. All four vaccine preparations were stored at 4° C. for two years. At different points during the storage (0, 6, 12 or 24 months), all four formulations were used to vaccinate three months old cows.

On days 0 and 21, three-month old cows were vaccinated through subcutaneous route with a 2 ml vaccine formulation. The serum from the vaccinated animals was collected on day 35, and serological response to the vaccine was measured in terms of the antibody titer through BVDV-E2 ELISA. As shown in FIG. 5, the microfluidized vaccine preparation showed a higher antibody titer at all the time points tested (0, 6, 12, and 24 months), suggesting the stability of the antigen preparation is not lost during the intrinsic incorporation of the antigen during the microfuidization process. Moreover, it was also surprisingly found that the microfluidized vaccine preparation induced an enhanced immune response at all time points.

EXAMPLE 9

Reduction in the Vaccine-Induced Increase in Rectal Temperature after Microfluidization The microfluidized and non-microfluidized vaccine preparations made as described in Example 7 were used to vaccinate the cattle on day zero and the rectal temperature was monitored during the period from one day prior to vaccination till four days post vaccination. The vaccine dose was 2 ml. The groups were vaccinated either with a single or double dose of the vaccine. Rectal temperatures were measured and recorded daily on Day-1 through Day 4, inclusive. Rectal temperatures on day 0 were measured prior to administration of test article.

As shown in FIG. 6, the results indicate that there was a steep rise in the rectal temperature in about 24 hours following vaccination in those animals vaccinated with either a single or double dose of the non-microfluidized vaccine formulation. However, in the animals vaccinated with microfluidized forms of vaccine, the rise in rectal temperature following the vaccination was only minimal and significantly lower than in the animals vaccinated with the non-microfluidized formulation (FIG. 6).

EXAMPLE 10

Figure 7:
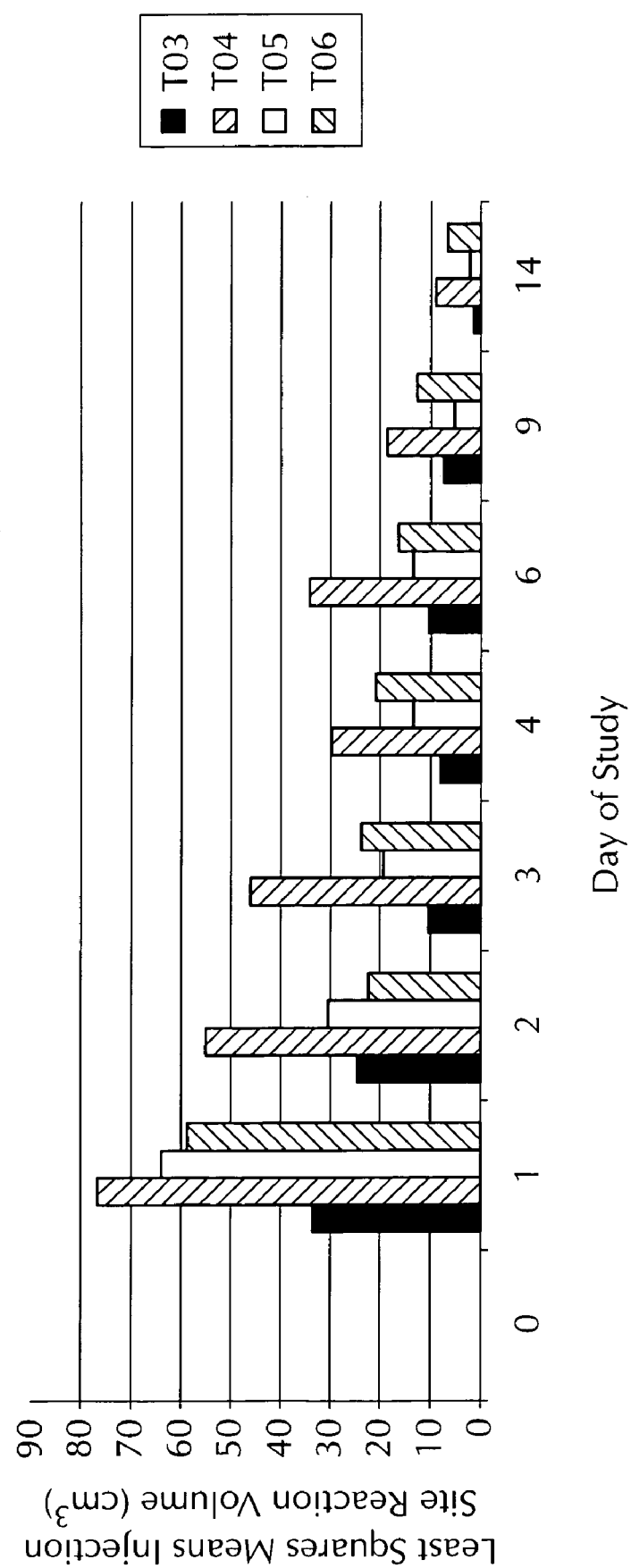
FIG. 7 depicts least squares mean injection site reaction volumes observed in cattle following administration of non-microfluidized and microfluidized vaccine formulations. T03: Non-microfluidized formulation—Single Dose; T04: Non-microfluidized formulation—Double dose; T05: Microfluidized formulation—Single Dose; T06: Microfluidized formulation—Double dose.

The Injection Site Reaction Volume was Resolved Faster when Vaccinated with Microfluidized Vaccine Formulations The microfluidized and non-microfluidized vaccine preparations made as described in the Example 7 were used to vaccinate the cattle on day zero. The animals included in this study were cross-bred beef cattle. There were three animals in each of the placebo treatment groups (T01 and T02). There were six animals in each of the groups T03 through T06. The vaccine dose was 2 ml and the groups were vaccinated either with one or two doses of the vaccine on day zero. On day 0, test article was administered in the right neck. Animals receiving the double dose (4 ml) of the test article (T02, T04, and T06) received the entire double dose as a single injection at one side. Observation of injection sites, including estimation of reaction size at the injection site were made on the right side of the neck on Day 0 through Day 4, inclusive, and Days 6, 9, and 14. On Day 0 injection sites were observed prior to administration of test articles. The groups vaccinated with one or two doses of the placebo did not show any significant increase in the injection site reaction volume and therefore those data are not shown in the FIG. 7. In the case of the non-microfluidized vaccine formulation, there was a proportional increase in the injection site reaction volume between the one dose and two dose vaccination. On the other hand, in the case of the microfluidized vaccine formulation, although the single dose induced a larger injection site reaction volume, the injection with second dose did not cause any further increase. Moreover, in the case of the animals injected with microfluidized vaccine formulation, the injection site reaction site volume was resolved at a faster rate when compared to that in the animals injected with a non-microfluidized vaccine formulation. These results are shown in FIG. 7.

EXAMPLE 11

Preparation of Microfluidized AMPHIGEN® Formulation-Based Vaccine Preparations with Intrinsically Incorporated BVD Viral and Leptospira Antigens and Immunostimulatory Molecules such as Quil A and DDA Formalin-inactivated Leptospira hardjo-bovis strain CSL was formulated in the appropriate adjuvant at direct counts of about $1.4 \times 10^9$ organisms/5 ml dose. Formalin-inactivated Leptospira Pomona strain T262 was formulated at about 2400 Nephalomeric Units/5 ml dose. Nephalomeric units were calculated based on nephalometric measurement of preprocessed fermentation fluid. BVD virus Type 1 was formulated at E2 Elisa titer of about 3000 Relative Units/5 ml dose. BVD virus Type 2 was formulated at E2 Elisa titer of about 3500 Relative Units/5 ml dose. The Relative Unit was calculated based on the E2 ELISA titer of pre-assembly post-inactivation bulk fluid. Both Quil-A and cholesterol were used at the concentration of 0.5 mg per dose. Thimerosol and the AMPHIGEN® formulation were used at the final concentration of 0.009% and 2.5%, respectively. Aluminum hydroxide (Rehydragel LV) was used at the final concentration of 2.0%. When DDA was used as an immunomodulator, DDA was included within the AMPHIGEN® formulation. The AMPHIGEN® formulation (i.e., the 40% Drakeol-lecithin stock solution) contained 1.6 mg/ml of DDA and, when appropriately diluted, the final vaccine preparation contained 2.5% AMPHIGEN® formulation and 0.1 mg/ml of DDA.

In the preparation of different vaccine formulations, BVD fractions, Leptos, Quil-A, chloestrol, thimerosol, the AMPHIGEN® formulation, and saline as an extender were added to a Silverson homogenizer and mixed for 15 minutes at 10,000±500 RPM. Components were then microfluidized through a 200 micron screen at 10,000 psi.

When the vaccine formulation contained aluminum hydroxide, the microfluidization was carried out without aluminum hydroxide. After the microfluidization was completed, aluminum hydroxide was added and mixed with a stir bar overnight at 4° C.

EXAMPLE 12

Preparation of BVD Viral Vaccine for Challenge Studies

The vaccine preparation used in this experiment contained antigens from both BVD virus Type 1 and BVD Virus Type 2. BVD1-5960 antigen was used at the post-inactivation ELISA titer of 2535 RU/dose for gp53. BVD2-890 antigen was used at the post-inactivation ELISA titer of 3290 RU/dose for gp53. Quil A and cholesterol were used at the concentration of 0.5 mg/ml. Thimersol and the AMPHIGEN® formulation were used at the final concentration of 0.009% and 2.5%, respectively. When DDA was used as an immune modulator, DDA was included within the the AMPHIGEN® formulation. The AMPHIGEN® stock solution (40% Drakeol-lecithin solution) contained varying amounts of DDA and when appropriately diluted, the final vaccine preparation contained 2.5% AMPHIGEN® formulation and DDA concentration ranging from 0.5 mg/dose to 2.0 mg/dose. Aluminum gel (Rehydragel-LV) was used at the final concentration of 2%. GPI-0100 was used in the range of 2, 3, and 5 mg/dose.

All the components were added to a Silverson homogenizer and blended for 15 minutes at 10,500 rpm and then microfluidized by passing through a 200 micron chamber with 10,000 psi. When the vaccine preparation contained aluminum hydroxide, the microfluidization was carried out without aluminum hydroxide. After the microfluidization was completed, aluminum hydroxide was added and mixed with a stir bar overnight at 4° C.

EXAMPLE 13

Protection Against Leptospira Challenge After Vaccination with a Microfluidized Amphigen Vaccine Formulation with Leptospira Antigens

TABLE 1

Treatment Groups

| Treatment group | Composition of adjuvant |
| --- | --- |
| T01 | Saline |
| T02 | Quil-A, Cholesterol, and the AMPHIGEN ® formulation (QAC) |
| T03 | Quil-A, Cholesterol, the AMPHIGEN ® formulation and AIOH (QAC-AIOH) |
| T04 | DDA, Cholesterol, and the AMPHIGEN ® formulation (DDA) |
| T05 | DDA, Cholesterol, the AMPHIGEN ® formulation, and AIOH (DDA-AIOH) |

Table 1 shows the composition of the adjuvant formulations in the vaccine preparations tested in this study. The vaccine preparations were prepared as described in the Example 11. There were six animals in each group. About seven-month old beef cross-bred heifers were used in this study. Vaccination was done on Day 0 and Day 21 through subcutaneous route with 5 ml vaccine volume. Challenge was done with *L. hardjo*-bovis strain 203 from NADC (National agricultural Disease Center). Challenge was done during Days 57–59 with a 1-ml innoculum. Challenge was administered conjunctively in the eye and vaginally. The challenge material contained $5.0 \times 10^6$ leptospires/ml. Urine was collected weekly for lepto culture, FA and PCR. Kidney collection was made during Days 112 and 113.

TABLE 2

Results of the Leptospira Challenge Study

| Treatment | Percent calves ever positive for Leptospira in urine and Kidney through Culture | Percent of calves ever positive for Leptospira in urine and Kidney through FA | Percent of calves ever positive for Leptospira in urine and Kidney through PCR | Percent of Calves ever positive for Leptospira in Urine and Kidneys across all assays |
|---|---|---|---|---|
| Saline | 100 | 83.3 | 83.3 | 100 |
| QAC | 0 | 0 | 0 | 0 |
| QAC/AlOH | 0 | 50.0 | 0 | 50.0 |
| DDA | 0 | 0 | 0 | 0 |
| DDA/AlOH | 0 | 33.3 | 16.7 | 50.0 |

Table 2 shows the data from the Leptospira challenge study. In determining the percentage of Leptospira infection in the challenged animal, the following criteria were used. If the kidney culture was positive for only one sample, the animal is considered to be positive for Leptospira. If an animal is positive in only one sample for either FA or PCR, the animal is considered to be negative. If the sample is positive for both FA and PCR in only one sample, it was considered positive for Leptospira.

The results shown in Table 2 indicate that there was a significant shorter duration of urinary shedding in all vaccine groups based on all the three assays. As far as urinary and kidney colonization are concerned, the efficacies of the QAC- and DDA-containing formulations without AlOH were comparable. AlOH did not improve and even reduced the efficacies of the QAC- or DDA-containing vaccines in this challenge study.

TABLE 3

Microscopic Agglutination Titer Range
On Day Of Peak Geometric Mean Titer Prior To Challenge (Day 35)

| Treatment | *L. Hardjo* | *L. pomona* |
|---|---|---|
| Saline | <20 | <20 |
| QAC | 160–640 | 1280–10240 |
| QAC/AlOH | 160–2560 | 8–10240 |
| DDA | 40–1280 | 320–2560 |
| DDA/AlOH | 320–640 | 1280–5120 |

Serological responses against both of the Leptospira antigens in the vaccine formulation were detected in the vaccinated animal and the peak response was noted on Day 35. There was no correlation between the serological response and the protection against the challenge. The presence of aluminum gel in the vaccine formulation reduced the level of protection although the serological response was enhanced by the presence of aluminum gel in the vaccine.

EXAMPLE 14

Elicitation of Immune Response to the BVD Viral Antigen and Protection Against the BVD Type 2 Virus Challenge After Immunization with a Microfluidized Vaccine Preparation Containing AMPHIGEN® Formulation and DDA Four to seven month-old seronegative calves were used in this experiment. There were six different groups and each group had ten animals (Table 4). On Day 0 and Day 21 each animal received one 2 ml subcutaneous dose of the vaccine or placebo in the lateral neck approximately midway between the scapula and poll.

TABLE 4

Treatment Groups

| Treatment | Adjuvant composition |
|---|---|
| T01 | Saline |
| T02 | Quil-A, AMPHIGEN ® formulation, and Chloesterol |
| T03 | AMPHIGEN ® formulation, Choloesterol, DDA (0.5 mg/dose) and AlOH |
| T04 | AMPHIGEN ® formulation, Cholesterol, and DDA (0.5 mg/dose) |
| T05 | AMPHIGEN ® formulation, Cholesterol, and DDA (1.0 mg/dose) |
| T06 | AMPHIGEN ® formulation, Cholesterol, and DDA (2.0 mg/dose) |

A 5 ml dose of the challenge virus preparation (approximately 2.5 ml per nostril) was administered intranasally on Day 44 of the study. Noncytopathic BVD virus Type 2, isolate # 24515 (Ellis Strain), lot # 46325-70 was used in this study as the challenge strain. Retained samples of challenge material were tittered (two replicates per titration) at the time challenge was initiated and immediately upon its completion. The mean live virus titer per 5 ml dose was 5.3 $\log_{10}$ FAID$_{50}$/5 ml prior to challenge and 5.4 $\log_{10}$ FAID$_{50}$/5 ml post challenge (FAID is equivalent to TCID$_{50}$).

Animals were monitored daily from Day-3 through Day 58. Clinical disease scores of 0, 1, 2, or 3, based on clinical signs attributable to BVD 2 infection were made for each animal on Days 42 through 58. The scores on Day 44 were recorded prior to challenge. Blood samples (two 13 ml Serum Separation Tubes, SST) were collected from each animal on Days 0, 21, 35, 44, and 58 for determination of serum titers of BVD Type 1 and BVD Type 2 virus neutralization antibodies.

Blood samples were collected from each animal on Days 42 through Day 58, inclusive, and the presence of BVD virus in buffy coat cell was determined. On Day 44, samples were obtained prior to challenge.

For determining white blood cell counts, blood samples (one 4 ml EDTA tube) were collected from each animal on Day 42 through Day 58, inclusive. On Day 44, samples were obtained prior to challenge.

Leukopenia was defined as a 40% or greater decrease in the WBC count from baseline (average of pre-challenge WBC counts from two days prior to, and the day of challenge).

Clinical disease scores were used to define disease status as follows; if the score is ≦1, then disease=no; if the score is >2, then disease=yes.

As shown in the Tables 5 and 6, the groups vaccinated with vaccines containing BVD viral antigens along with the AMPHIGEN® formulation, Quil A or DDA and microfluidized, seroconverted with significant serum virus neutralization titers for both BVD Type 1 and BVD Type 2 viruses. In those groups there was also a significant reduction in the percentage of animals showing viremia following challenge, while in the control group 100% of the animals were viremic (Table 7). In addition, in those vaccinated groups the frequency of the disease was also significantly reduced (Table 8). Similarly, the percentage of animals showing leukopenia was also reduced in the vaccine groups and the reduction of leukopenia was more significant in the group containing DDA than in the group containing Quil A (Table 9). In the control group there was a significant drop in the weight gain when compared to the vaccinated groups. (Table 10)

Serology

Prior to vaccination on Day 0, all animals in the study were seronegative (SVN<1:2) for antibodies to BVD virus Types 1 and 2 (data not shown). Fourteen days after the second vaccination (Day 35), all animals that were administered the placebo (T01) remained seronegative for antibodies to BVD virus Types 1 and 2; and all of the animals vaccinated with the ITAs (Investigational Test Antigen) (T02, T03, T04, T05 and T06) were seropositive (SVN≧1:8) for antibodies to BVD virus, Types 1 and 2. One animal which was administered with the vaccine adjuvanted with the AMPHIGEN® formulation at 2 mg/dose of DDA had an SVN titer of 3 for antibodies to BVD virus Type 2 on Day 35 (Table 11 and 12).

Prior to challenge on Day 44, all controls (T01), except one, were seronegative (SVN<1:2) for antibodies to BVD virus Types 1 and 2 (data now shown). The one control (#2497) was seropositive (SVN=10) for antibodies to BVD virus Type 1 and seronegative for antibodies to BVD virus Type 2. Fourteen days following challenge, all animals in the study were seropositive for antibodies to BVD virus Types 1 and 2.

TABLE 5

BVD Virus Type 1 Geometric Mean Serum Virus Neutralization Titers

| | | BVDv Type 1 Geometric Mean SVN Titers on Study Day | | | | |
|---|---|---|---|---|---|---|
| | Treatment | 0 | 21 | 35 | 44 | 58 |
| T01 | Saline | <2 | <2 | <2 | <2 | 23.9 |
| T02 | Amphigen, Quil A | <2 | 39.1 | 19824.5 | 14018.2 | 27554.5 |

TABLE 5-continued

BVD Virus Type 1 Geometric Mean Serum Virus Neutralization Titers

| | | BVDv Type 1 Geometric Mean SVN Titers on Study Day | | | | |
|---|---|---|---|---|---|---|
| | Treatment | 0 | 21 | 35 | 44 | 58 |
| T03 | Amphigen, 0.5 mg DDA, Al | <2 | 51.8 | 32204.8 | 22381.1 | 23170.4 |
| T04 | Amphigen, 0.5 mg DDA | <2 | 27.0 | 14512.4 | 8932.0 | 21996.2 |
| T05 | Amphigen, 1.0 mg DDA | <2 | 26.7 | 11585.2 | 8194.6 | 20882.0 |
| T06 | Amphigen, 2.0 mg DDA | <2 | 23.5 | 8778.7 | 6769.3 | 16961.1 |

TABLE 6

BVD Virus Type 2 Geometric Mean Serum Virus Neutralization Titers

| | | BVDv Type 1 Geometric Mean SVN Titers on Study Day | | | | |
|---|---|---|---|---|---|---|
| | Treatment | 0 | 21 | 35 | 44 | 58 |
| T01 | Saline | <2 | <2 | <2 | <2 | 522.0 |
| T02 | Amphigen, Quil A | <2 | 8.9 | 2272.4 | 2048.2 | 24833.6 |
| T03 | Amphigen, 0.5 mg DDA, Al | <2 | 9.5 | 3565.7 | 2702.2 | 20881.8 |
| T04 | Amphigen, 0.5 mg DDA | <2 | 4.1 | 1260.7 | 989.1 | 18496.2 |
| T05 | Amphigen, 1.0 mg DDA | <2 | 6.4 | 1398.8 | 1453.9 | 30047.8 |
| T06 | Amphigen, 2.0 mg DDA | <2 | 7.7 | 1673.2 | 1428.9 | 16384.0 |

TABLE 7

BVD Virus Isolation Following Challenge

| | | BVD Virus Isolation | | |
|---|---|---|---|---|
| Treatment | On Study Days | | Frequency (%) of Viremic Animals | LSMean Days with Viremia |
| T01 Saline | 47 through 58 | | 10/10 (100.0) | 10.4 |
| T02 Amphigen, Quil A | 50 through 53 | | 1/10 (10.0) | 0.4 |
| T03 Amphigen, 0.5 mg DDA, Al | — | | 0/10 (0.0) | 0.0 |
| T04 Amphigen, 0.5 mg DDA | 48, 50 through 52, 57 | | 3/10 (30.0) | 0.5 |
| T05 Amphigen, 1.0 mg DDA | 49 through 51 | | 2/10 (20.0) | 0.4 |
| T06 Amphigen, 2.0 mg DDA | 48 through 52 | | 2/10 (20.0) | 0.5 |

TABLE 8

Clinical Signs Of BVD Disease Following Challenge

| Treatment | | Frequency (%) with Disease | Frequency (%) Observations with Clinical Sign of BVD Disease | | | | Total Obs. |
|---|---|---|---|---|---|---|---|
| | | | 0 | 1 | 2 | 3 | |
| T01 | Saline | 9/10 (90.0) | 75 (46) | 63 (37.5) | 29 (17.3) | 1 (0.6) | 168 |
| T02 | Amphigen, Quil A | 1/10 (10.0) | 105 (61.8) | 63 (37.1) | 2 (1.2) | 0 (0) | 170 |
| T03 | Amphigen, 0.5 mg DDA, Al | 2/10 (20.0) | 99 (58.2) | 67 (39.4) | 4 (2.4) | 0 (0) | 170 |
| T04 | Amphigen, 0.5 mg DDA | 0/10 (0.0) | 118 (69.4) | 52 (30.6) | 0 (0) | 0 (0) | 170 |
| T05 | Amphigen, 1.0 mg DDA | 0/10 (0.0) | 101 (59.4) | 69 (40.6) | 0 (0) | 0 (0) | 170 |
| T06 | Amphigen, 2.0 mg DDA | 0/10 (0.0) | 104 (61.2) | 66 (38.8) | 0 (0) | 0 (0) | 170 |

TABLE 9

Leukopenia Following Challenge

| Treatment | | Leukopenia | |
|---|---|---|---|
| | | Frequency (%) of Leukemic Animals | LSMean Days with Leukemia |
| T01 | Saline | 10/10 (100.0) | 7.8 |
| T02 | Amphigen, Quil A | 6/10 (60.0) | 1.2 |
| T03 | Amphigen, 0.5 mg DDA, Al | 2/10 (20.0) | 0.2 |
| T04 | Amphigen, 0.5 mg DDA | 4/10 (40.0) | 0.8 |
| T05 | Amphigen, 1.0 mg DDA | 3/10 (30.0) | 0.9 |
| T06 | Amphigen, 2.0 mg DDA | 2/10 (30.0) | 0.5 |

TABLE 10

Body Weight and Body Weight Gain During the Study

| Treatment | | Mean Body Weight (lb.) on Study Day | | | | Weight Gain (lb) |
|---|---|---|---|---|---|---|
| | | −1 | 43 | 50 | 58 | |
| T01 | Sailne | 378.0 | 484.9 | 491.0 | 476.9 | 98.9 |
| T02 | Amphigen, Quil A | 428.0 | 526.5 | 546.7 | 579.0 | 151.0 |
| T03 | Amphigen, 0.5 mg DDA, AlOH | 410.5 | 514.4 | 534.2 | 579.0 | 168.5 |
| T04 | Amphigen, 0.5 mg DDA | 373.7 | 472.3 | 492.6 | 538.1 | 164.4 |
| T05 | Amphigen, 1.0 mg DDA | 358.9 | 451.4 | 478.9 | 507.1 | 148.2 |
| T06 | Amphigen, 2.0 mg DDA | 408. | 513.3 | 533.9 | 560.3 | 151.6 |

Virus Isolation

As the data shown in Table 13, during the challenge period (Days 44 through 58), all ten animals in the control (T01) were viremic (BVD virus was isolated on one or more days). In the groups administered with the ITAs, the frequency of viremic animals was one, zero, three, two and two in each group of ten (T02, T03, T04, T05 and T06, respectively). The difference between the control and the groups administered with the ITAs was statistically significant ($P \leq 0.05$). The least squares mean number of days of viremia was also significantly greater (10.4 days) for the control as compared to the groups administered with the ITAs (0.0 to 0.5 days).

Clinical Disease

Animals with clinical sign scores of 2 or 3 were considered demonstrating signs of BVD disease. As shown in the Table 14, the frequency of animals with clinical signs of BVD virus disease was nine of ten in the control (T01) and one, two, zero, zero and zero of ten in each of the groups administered the ITAs (T02, T03, T04, T05 and T06, respectively). The difference between the control and groups that were administered the ITAs was statistically significant ($P \leq 0.05$).

Leukopenia

As shown in Table 15, during the challenge period (Days 44 through 58), all ten animals in the control (T01) were leukemic (a 40% reduction in white blood cell count from pre-challenge baseline, Days 42–44). The frequency of animals with leukemia was six, two, four, three and two of the ten animals in each of the groups administered with the ITAs (T02, T03, T04, T05 and T06, respectively). The difference between the control and the group administered with vaccine which was adjuvanted with the AMPHIGEN® formulation at 0.5 mg/dose and aluminum hydroxide (T03) was statistically significant ($P \leqq 0.05$). The least squares mean number of days of leukemia was significantly greater (7.8 days) for the control as compared to the groups administered with the ITAs (0.2 to 1.2 days).

EXAMPLE 15

Elicitation Of Immune Response To The BVD Viral Antigen And Protection Against The BVD Type 2 Virus Challenge After Immunization With Microfluidized Vaccine Formulation Containing GPI-0100

A set of experimental conditions as described in the Example 14 was followed and a direct comparison between Quil A and GPI-0100 was made. As shown in the Tables 11 and 12 , the animals vaccinated with BVD antigens in the microfluidized AMPHIGEN® formulation-based preparation containing either Quil A or GPI-0100 had a significant antibody titer both for BVD Type 1 and BVD Type 2 viruses. The antibody titer for BVD Type 1 virus was much more higher than that for BVD Type 2 virus. However, subsequent challenge with BVD Type 2 virus showed a strong protection and the disease incidence was significantly reduced in the calves vaccinated with the microfluidized AMPHIGEN® formulation-based vaccine preparation containing GPI-0100.

TABLE 11

BVD virus Type 1 Geometric Mean Serum Virus Neutralization Titers

| | | Geometric mean SVN titer | | | | |
|---|---|---|---|---|---|---|
| Treatment | | 0 | 21 | 35 | 43 | 57 |
| T01 | Saline | <2 | <2 | <2 | <2 | 35.5 |
| T02 | Amphigen, Quil A | <2 | 98.7 | 20171.0 | 12203.4 | 44762.4 |
| T03 | Amphigen, 2 mg GPI-0100, AIOH | <2 | 84.6 | 10998.5 | 7383.2 | 25709.2 |
| T04 | Amphigen, 2 mg GPI-0100 | <2 | 106.0 | 18179.2 | 8933.2 | 28526.2 |
| T05 | Amphigen, 3 mg GPI-0100 | <2 | 62.9 | 15024.3 | 8780.1 | 19824.4 |
| T06 | Am,phigen, 5 mg GPI-0100 | <2 | 71.1 | 12203.3 | 7512.0 | 16670.2 |

TABLE 12

BVD virus Type 2 Geometric Mean Serum Virus Neutralization Titers

| | | BVDv Type 1 Geometric Mean SVN Titers on Study Day | | | | |
|---|---|---|---|---|---|---|
| Treatment | | 0 | 21 | 35 | 44 | 58 |
| T01 | Saline | <2 | <2 | <2 | <2 | 14.7 |
| T02 | Amphigen, Quil A | <2 | 12.9 | 2312.0 | 1692.5 | 1663.4 |
| T03 | Amphigen, 2 mg GPI-0100, AIOH | <2 | 13.2 | 1663.5 | 1116.8 | 1562.3 |
| T04 | Amphigen, 2 mg GPI-0100 | <2 | 20.5 | 2610.2 | 1978.2 | 2478.7 |
| T05 | Amphigen, 3 mg GPI-0100 | <2 | 11.4 | 1752.8 | 1305.2 | 2435.4 |
| T06 | Amphigen, 5 mg GPI-0100 | <2 | 12.0 | 3158.4 | 2120.2 | 1845.6 |

TABLE 13

BVD Virus Isolation Following Challenge

| | | BVD Virus Isolation | |
|---|---|---|---|
| Treatment | | Frequency (%) of Viremic Animals | LSMean Days with Viremia |
| T01 | Saline | 10/10 (100.0) | 8.4 |
| T02 | Amphigen, Quil A | 3/10 (30.0) | 0.3 |
| T03 | Amphigen, 2 mg GPI-0100, AIOH | 0/10 (0.0) | 0.0 |
| T04 | Amphigen, 2 mg GPI-0100 | 1/10 (10.0) | 0.1 |
| T05 | Amphigen, 3 mg GPI-0100 | 3/10 (30.0) | 0.3 |
| T06 | Amphigen, 5 mg GPI-0100 | 2/10 (20.0) | 0.2 |

TABLE 14

Clinical Signs of BVD Disease Following Challenge

| | | Frequency (%) with Disease | Frequency (%) Observations with Clinical Disease Score of | | | Total Obs. |
|---|---|---|---|---|---|---|
| | Treatment | | 0 | 1 | 2 | |
| T01 | Saline | 5/10 (50.0) | 103 (60.6) | 55 (32.4) | 12 (7.1) | 170 |
| T02 | Amphigen, Quil A | 5/10 (50.0) | 115 (67.6) | 48 (28.2) | 7 (4.1) | 170 |
| T03 | Amphigen, 2 mg GPI-0100, AIOH | 0/10 (0.0) | 128 (75.3) | 42 (24.7) | 0 (0) | 170 |
| T04 | Amphigen, 2 mg GPI-0100 | 0/10 (0.0) | 124 (72.9) | 46 (27.1) | 0 (0) | 170 |
| T05 | Amphigen, 3 mg GPI-0100 | 0/10 (0.0) | 104 (61.2) | 66 (38.8) | 0 (0) | 170 |
| T06 | Amphigen, 5 mg GPI-0100 | 0/10 (0.0) | 128 (75.3) | 42 (24.7) | 0 (0) | 170 |

TABLE 15

Leukopenia Following Challenge

| | | Leukopenia | |
|---|---|---|---|
| Treatment | | Frequency (%) of Leukopenic Animals | LSMean Days with Leukopenia |
| T01 | Saline | 9/10 (90.0) | 8.7 |
| T02 | Quil A | 6/10 (60.0) | 1.6 |
| T03 | 2 mg GPI-0100, AIOH | 7/10 (70.0) | 2.6 |
| T04 | 2 mg GPI-0100 | 4/10 (40.0) | 1.5 |
| T05 | 3 mg GPI-0100 | 7/10 (70.0) | 2.6 |
| T06 | 5 mg GPI-0100 | 8/10 (80.0) | 2.9 |

In conclusion, safety of each vaccine was demonstrated by the absence of adverse reactions or mortality in the vaccinated animals. Potency of each vaccine was demonstrated by seroconversion (SVN antibody titers to BVD-1 and BVD-2>1:8) in 100% of the vaccinated animals. Satisfactory resistance to challenge was demonstrated by the vaccine adjuvanted with 2 mg GPI-0100 only.

EXAMPLE 16

Vaccine Preparation Containing Microencapsulated Antigen in Microfluidized Oil-in-Water Emulsion Three grams of Trehalose (Fluka) was added to water to get a stock of 333 mg/ml of Trehalose solution. Recombinant PauA antigen solubililzed in 0.8% SDS solution (SDS/rPauA) was added to Trehalose solution to get a final concentration of 494 µg rPauA/ml. In the next step 10 grams of polylactide glycolic acid (PLG-Resomer RE 503H, Boeringher Ingelheim) was dissolved in 200 ml Methylene Chloride (MeCl2). The resulting PLG/MeCl2 solution was combined with the SDS-rPauA/trehalose solution prepared in the first step. The combined solution was subjected to microfluidization using (Microfluidizer from Microfluidics Model M 110EH) and the microfluidized preparation was spray dried using (Temco Spray Dryer Model SD-05). The spray dried material was collected using a 500 micron screen.

The concentration of rPauA in this spray dried material was quantified using a Western blot analysis. 1.04 mg of spray-dried material was dissolved in 50 µl of acetone and centrifuged at 13,200 rpm at room temperature for 10 minutes. The supernatant was removed. The supernatantand the pellet fractions were dried in a biological safety hood for 2.5 hours. The pellet was resuspended in 47.43 µL of sample solution (25 µl of sample buffer+1 0 µl of reducing agent+65µl of water). The dried supernatant fraction was resuspended with 20 µl of sample solution. In the western analysis purified PauA was used as a standard to quantify the rPauA content of the spray dried material.

A 20% Manitol stock solution was prepared by dissolving 100 grams of mannitol (Sigma) in 500 ml of Water for Injection (WFI). Solution was heated to 40° C. with hot plate/stirrer and cooled to 30° C. Solution was sterile filtered through a 0.22 micron sterile filter (Millipore). 2.5% Carboxymethylcellulose solution was prepared by dissolving 12.5 grams of carboxymethyulcellulose (Sigma) in 500 ml of WFI and mixed overnight at 4° C. Solution was autoclaved at 121° C.

The powder resulting from spray drying was reconstituted in a solution containing 5% mannitol, 0.3% carboxymethyl cellulose, and 1:5000 of thimerosol. The final solution was aliquoted in to 3 ml vials and lyophilized using a Lyophilizer (USIFROID). The lyophilized powder represents the microencapsulated rPauA. The microencapsulated subunit protein antigen is resuspended in 2 ml of microfluidized oil-in-water emulsion containing an AMPHIGEN® formulation (such as the microfluidized emulsion described in Example 20) and used as a vaccine.

EXAMPLE 17

Preparation of Microfluidized Vaccine Formulation Containing Both Bacterial Whole Cell Antigen and Recombinant Protein Antigen in Oil-in-Water Emulsion Two vaccine preparations were made which contained both recombinant *Streptococcus uberis* PauA protein and *Escherichia coli* bacterial cells, added intrinsically to oil-in-water emulsions as described in Exapmles 2 and 3. The recombinant PauA antigen was at the concentration of 100 µg per dose and the *E. coli* cells were at the final count of $4\times10^9$ per dose. The emulsion adjuvant compositions of the two vaccine formulations are shown in the Table 16.

TABLE 16

Vaccine formulations containing both the recombinant protein and whole *E. coli* cells.

| Treatment | Antigen | Adjuvant |
|---|---|---|
| T01 | Placebo | Saline |
| T02 | Pau A/*E. coli* | SEAM-14 |
| T03 | Pau A/*E. coli* | 2.5% Amphigen, 0.5 mg GPI-0100, 0.5 mg cholesterol |
| T04 | Pau A/*E. coli* | 2.5% Amphigen, 0.5 mg dimethyldioctadecylammonium bromide (DDA), 0.5 mg cholesterol |

EXAMPLE 18

Figure 8:
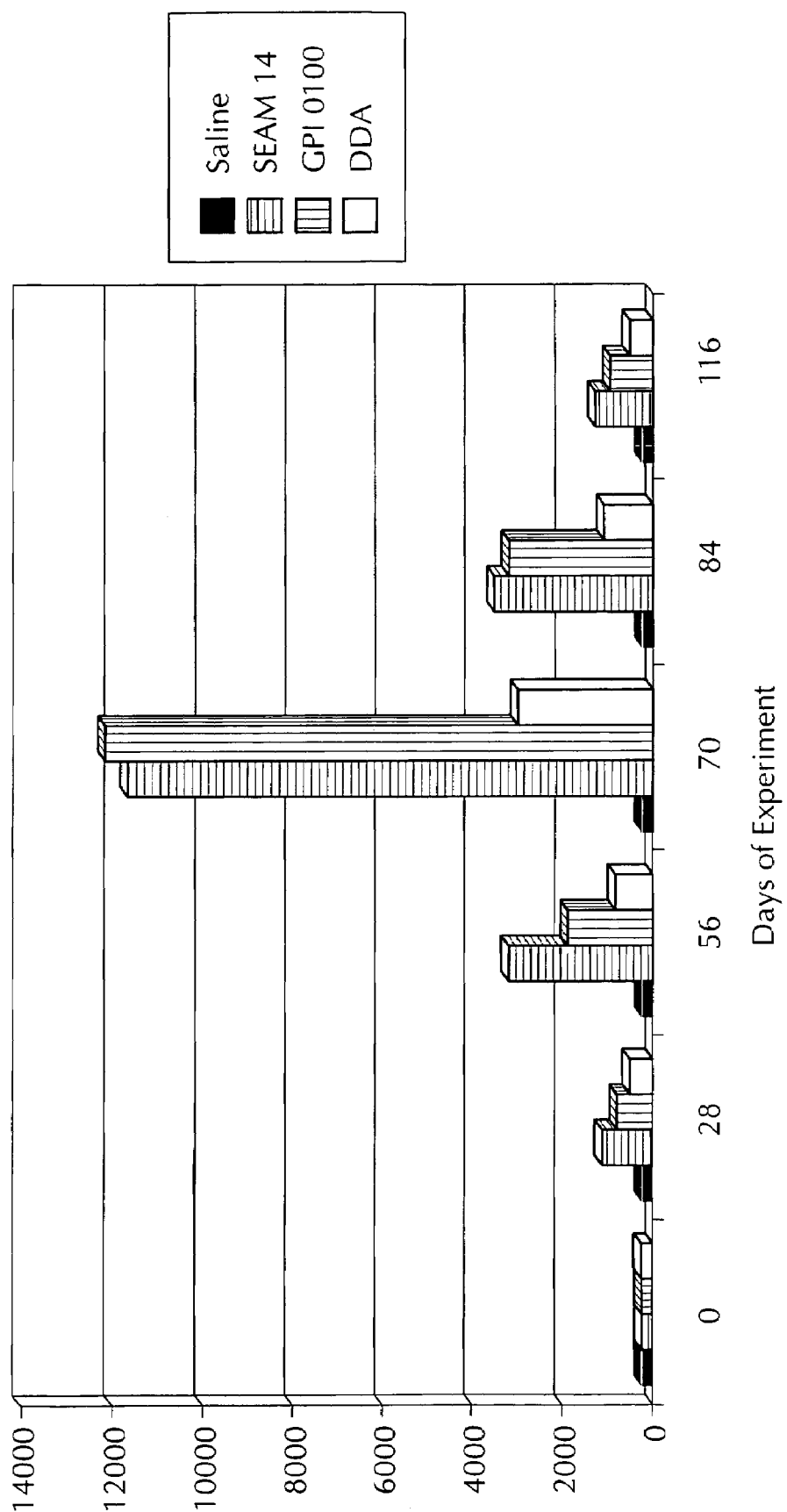
FIG. 8 depicts geometric mean IgG titers for recombinant PauA antigen from Streptococcus uberis after vaccination with the various vaccine formulations containing both recombinant PauA antigen and E. coli whole cell antigen.
Figure 9:
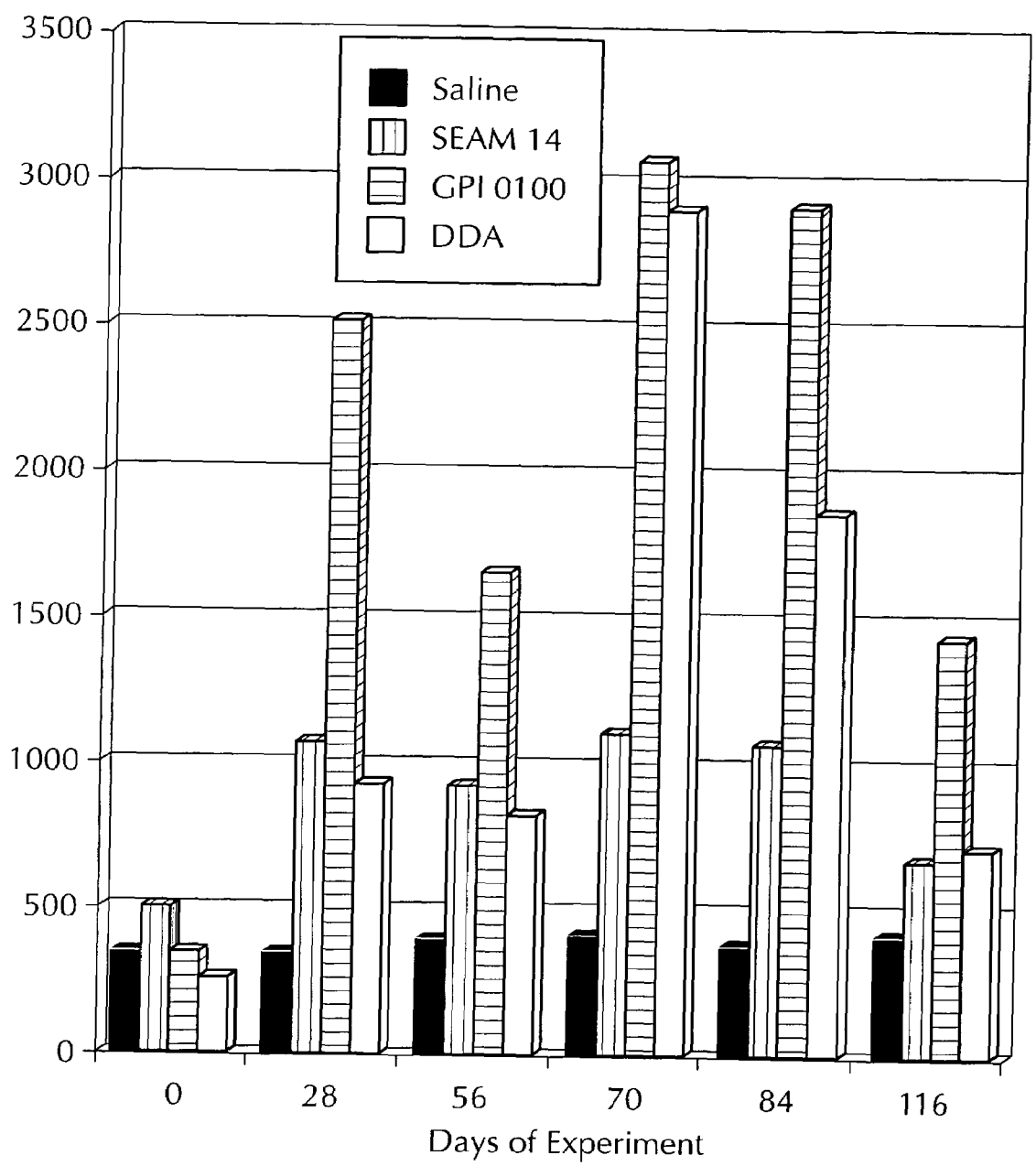
FIG. 9 depicts geometric mean IgG titers for E. coli whole cell antigen from Streptococcus uberis after vaccination with the various vaccine formulations containing both recombinant PauA antigen and E. coli whole cell antigen.
Figure 10A:
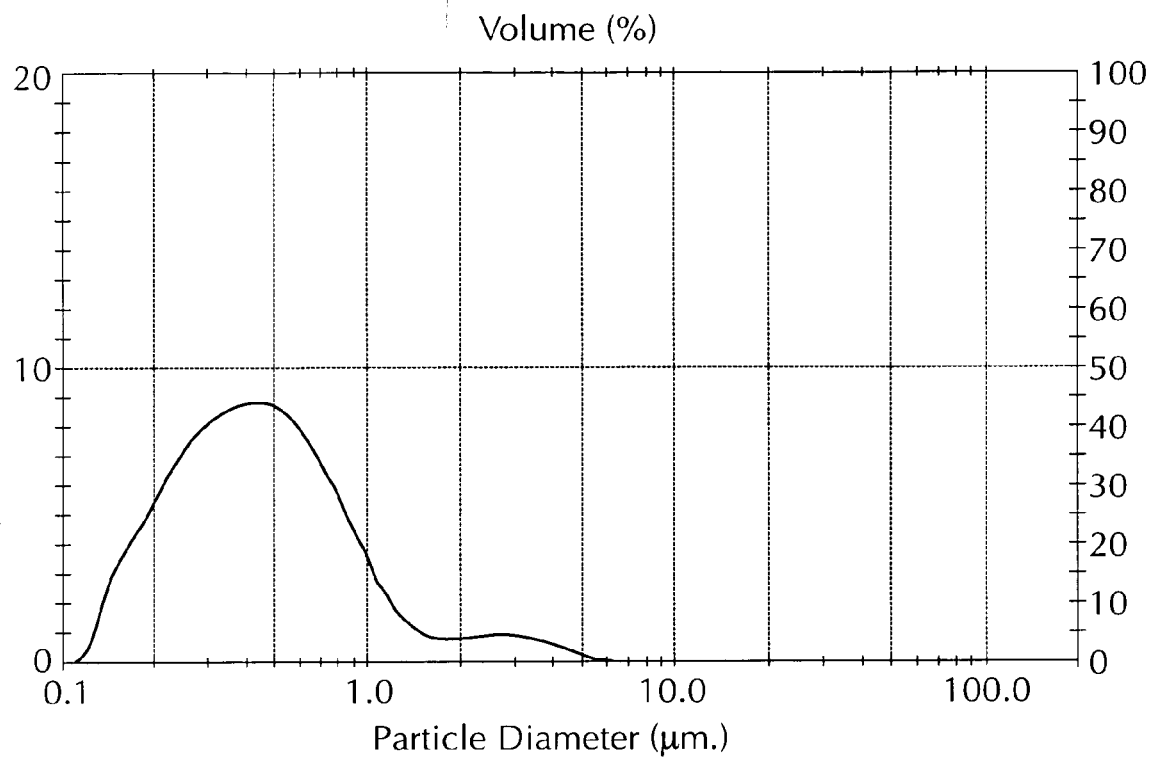
FIGS. 10A and 10B depict the particle size distribution of a Microfluidized Amphigen formulation at initial production (FIG. 10A) and at 22 months post production (FIG. 10B).
Figure 10B:
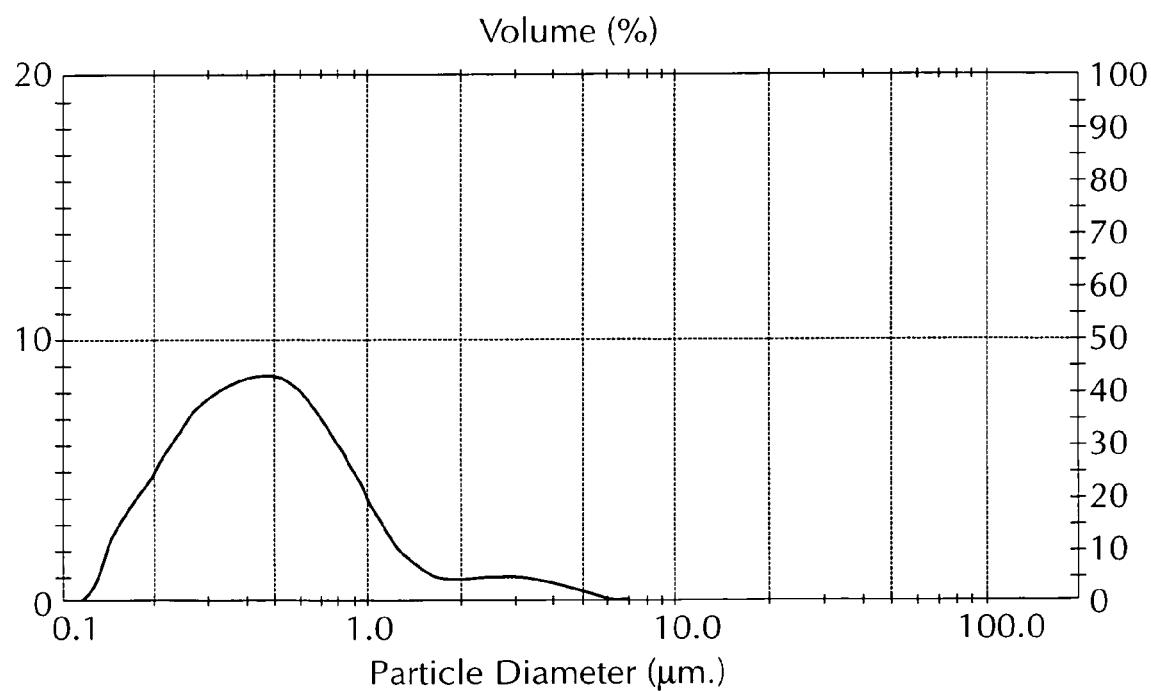
Figure 11:
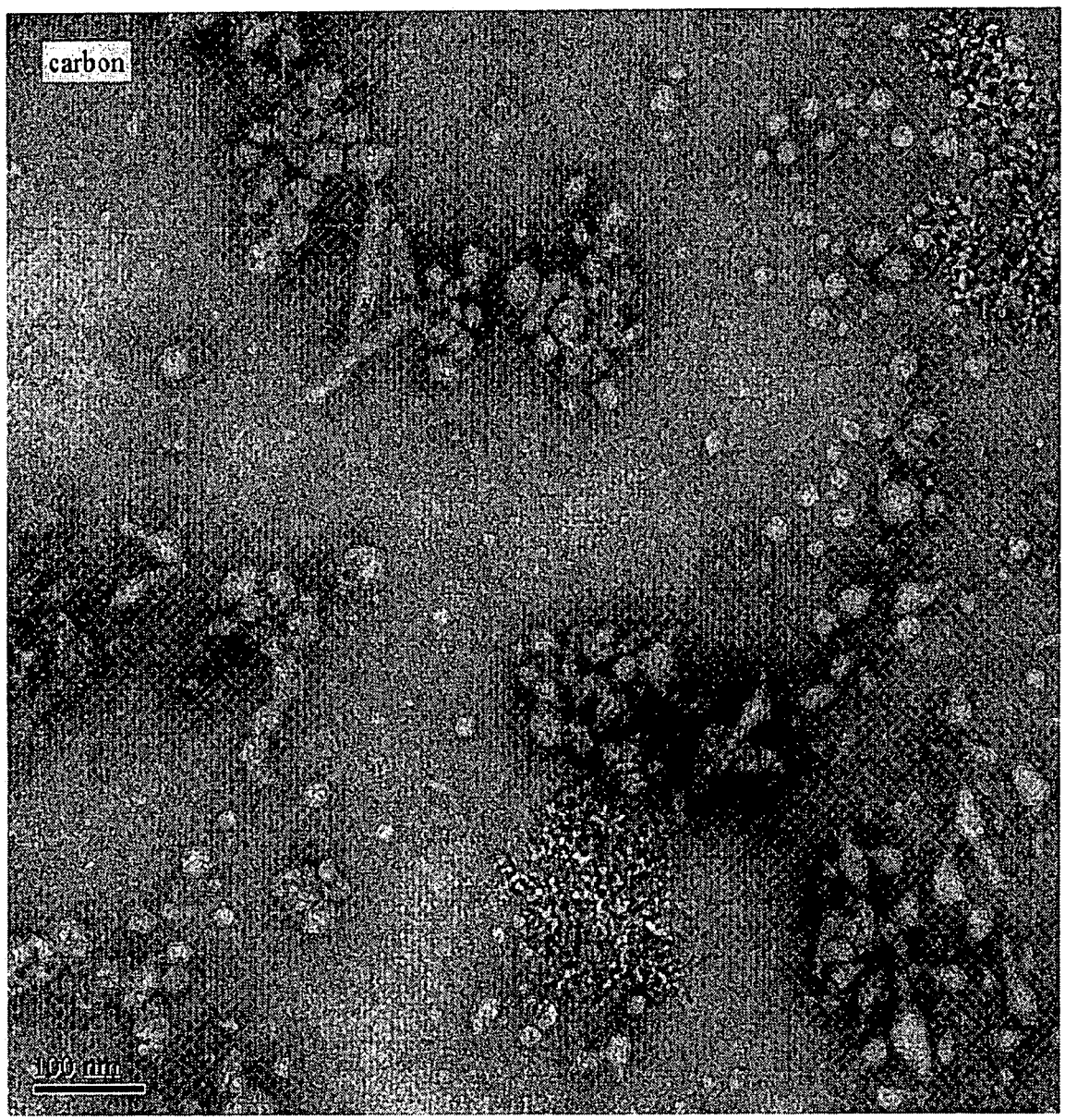
FIG. 11 is an electron microscopy photograph showing helical micelles formed with long with Quil A micelles and cholesterol crystals.
Figure 12:
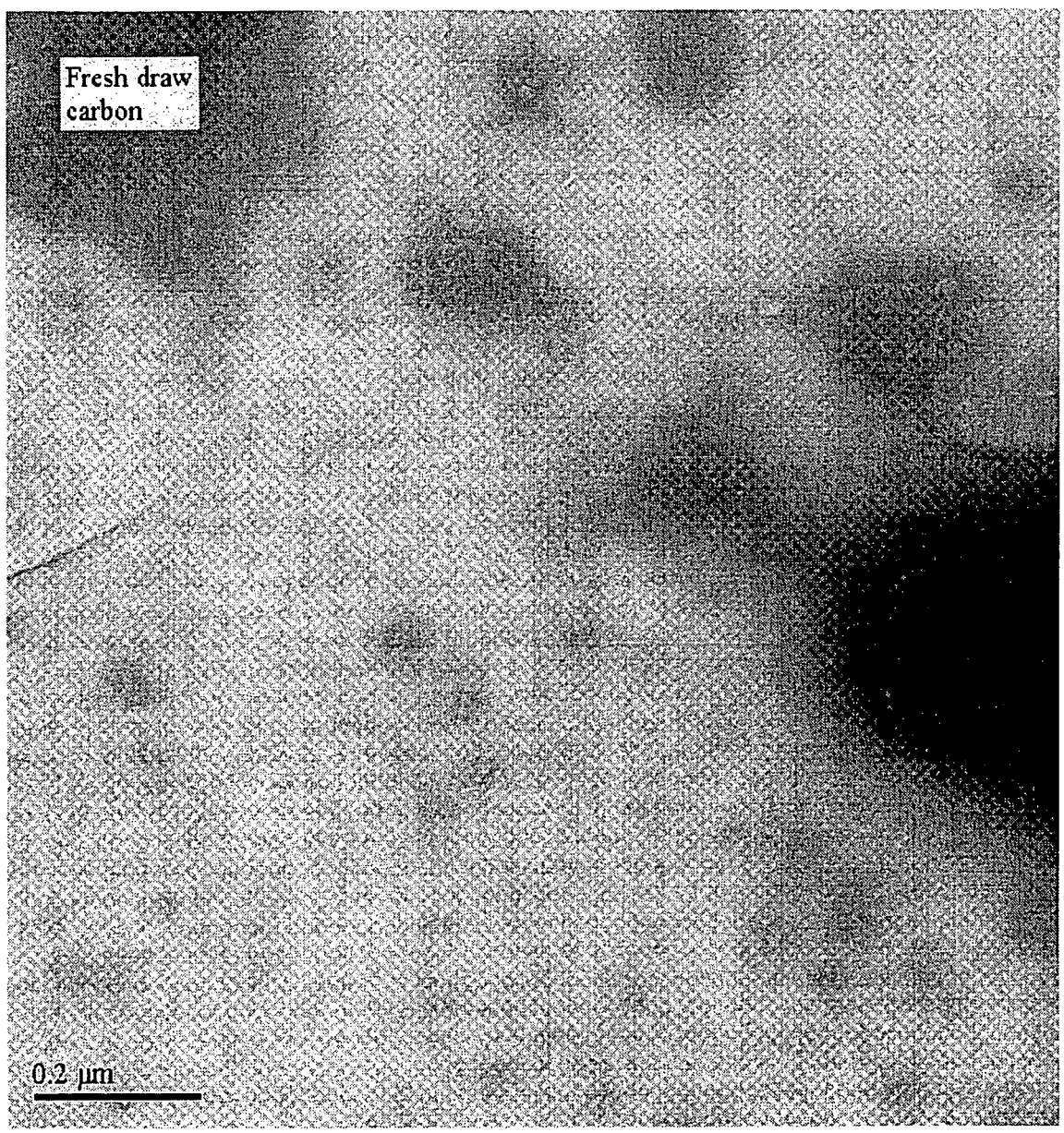
FIG. 12 is an electron microscopy photograph showing helical immunogenic complexes formed by Quil A and cholesterol on the surface of the BVD Type I antigen.

Immune Response to Microfluidized Vaccine Containing the rPauA and Whole Cell Bacterial Agents in Oil-in-Water Emulsion Mature dairy cows were used in this experiment. Animals were at the end of their first or second lactation at the time of enrollment. Two ml of each vaccine formulation was administered subcutaneously three times, once at the time of drying off (D-0), 28 days later (D=28), and again 4 to 10 days following calving (C+4–C+10). The first and third dose was administered on the left side of the neck and the second dose was administered on the right side of the neck. Blood was collected prior to each vaccination and approximately 14 days and 32 days following third vaccination. The antibody titer for *E. coli* and the rPauA antigen were determined through ELISA. As shown in FIG. 8, the results indicate that the antibody titer for rPauA was higher in the group vaccinated with vaccine formulation containing GPI-0100 as an immunostimulant and peaked on day 70 post initial vaccination. The antibody titer for *E. coli* antigen is shown in FIG. 9. The antibody titer for *E. coli* antigen was comparable in both vaccine formulations, although the presence of GPI-0100 as an immunostimulant induced a relatively higher antibody titer when compared to the formulation with DDA as an immunostimulant.

EXAMPLE 19

Analysis of Virucidal Activity of the Microfluidized AMPHIGEN® Formulation Based Vaccine Preparations In order to determine whether microfluidization inactivates the virus, the viricidal activity of three microfluidized AMPHIGEN® formulation based vaccine preparations were determined. The three preparations contained three different bovine infectious viruses, namely bovine herpes virus (BHV), parainfluenza virus 3 (PI3), and bovine respiratory synctial virus (BRSV).

Detection of the viricidal activity in the three vaccine preparations was conducted in accordance with the USDA 9CFR.113.35 requirements.

The results shown in Table 16 indicate that microfluidization of AMPHIGEN® formulation-based vaccine preparations does not cause any significant inactivation of the vaccine preparation.

TABLE 16

Analysis Of Viricidal Activities Of Microfluidized Vaccines

| Serial | BRSV | BHV | PI3 |
| --- | --- | --- | --- |
| A | 0 | 0.2 | 0 |
| AM200 | −0.2 | 0 | −0.2 |
| AM75 | 0 | −0.3 | −0.3 |
| AM75@37 C. | 0.1 | −0.3 | −0.2 |
| B | 0 | −0.1 | −0.2 |
| BM200 | 0 | 0 | −0.2 |
| BM75 | −0.2 | −0.5 | 0 |
| BM75@37 C. | 0.5 | −0.5 | 0 |
| C | 0.1 | −0.1 | −0.2 |
| CM200 | −0.2 | −0.1 | −0.2 |
| CM75 | 0.1 | 0.5 | −0.2 |
| CM75@37 C. | 0.5 | 0.5 | −0.2 |

A = Choloesterol added at 650 ml/min
B = Cholesterol added at 28 ml/mim
C = Cholesterol added at 5 ml/min
M200 = Microfluidized with 200 micron screen
M75 = Microfluidized with 75 micron screen
M75@37 C. = Fluids heated to 37° C. prior to microfluidization
A value above 0.7 is an indication of viricidal effect.

EXAMPLE 20

Preparation of a Microfluidized AMPHIGEN® Formulation

An AMPHIGEN® formulation was prepared by combining the DRAKEOL lecithin oil solution (light mineral oil with 25% lecithin) and TWEEN 80 (with the final concentration of 0.18%) and Span 80 (with the final concentration of 0.08%) with mixing for 8–22 hours at 36±1 ° C. The oil mixture was then added to saline with the aide of a Ross® (Hauppauge, N.Y. 11788) emulsifier at approximately 3400 rpm. Subsequently the mixture was passed once through a microfluidizer with a 200 μm interaction chamber at 4500±500 psi. FIG. 10 A and 10 B show the stability of the microfluidized AMPHIGEN® formulation. Particle size distribution, as measured by laser diffraction, at the starting, initial time point (FIG. 10A) was nearly identical to the particle size distribution after 22 months of 4° C. storage (FIG. 10B).

EXAMPLE 21

Electron Microscopic Analysis Of The Quil A—Cholesterol Immunogenic Complex

In order to determine the nature of the immunogenic complex formed by Quil A and cholesterol, a mixture of these two components was made either in the presence or absence of an antigen.

In a beaker containing 50 ml of KR-Hals buffer, BVD Type I antigen was added while stirring the solution with a magnetic bar. Afterwards, a concentrated stock solution of Quil A (50 mg/ml) was added drop wise while stirring the solution to achieve a final concentration of 50 μg/ml. The addition of Quil A was followed by the addition of a stock solution of cholesterol in ethanol (18 mg/ml) to the final concentration of 50 μg/ml.

In a second beaker, Quil A and cholesterol were added in the same way to the buffer of 50 ml without any BVD Type I antigen.

For transmission electron microscopy, 10 μl of each sample was adsorbed onto 400 mesh copper grids with a formvar/carbon support platform (Electron Microscopy Sciences, Inc., Fort Washington, Pa.). The samples were negatively stained using 10 μl of filtered 2% phosphotungstic acid, pH 5.2 as a contrast agent. The samples were examined using a JEOL 1230 Transmission electron Microscope (JEOL Inc., Tokyo, Japan) at 80 kV accelerating voltage. Digital imaging was performed on a Gatan BioScan 792 camera. Film microscopy was done on 4489 EM film and printed to Kodabrome II RC F3 paper (Eastman Kodak Company, Rochester, N.Y.)

In the solution containing only cholesterol and Quil A without any BVD Type I antigen, helical micelles were detected along with Quil A micelles and cholesterol crystals (FIG. 11). The helical micelles were intertwined and appeared like a mesh. In the sample containing the BVD Type I antigen, the helical micelles were found to encircle randomly certain dense areas (FIG. 12). The dense areas represent the BVD Type 1 antigen and the helical immunogenic complex resulting from the association of Quil A and cholesterol is found adsorbed on the surface of the BVD Type I antigen.

What is claimed is:

1. A vaccine comprising a saponin glycoside, a sterol and an antigen, wherein said saponin glycoside and said sterol associate with each other to form complexes in the form of helical micelles, and wherein said antigen is in admixture with, but not integrated within, said helical micelles.

2. The vaccine composition of claim 1, further comprising a veterinarily-acceptable carrier.

3. The vaccine composition of claim 2, wherein said veterinarily-acceptable carrier is an oil-in-water emulsion.

4. The vaccine composition of claim 1, wherein said saponin glycoside is a triterpenoid.

5. The vaccine composition of claim 4, wherein said triterpenoid is Quil A.

6. The vaccine composition of claim 1, wherein said sterol is cholesterol.

7. The vaccine composition of claim 1, wherein said antigen comprises a viral antigen, a bacterial antigen, or a combination thereof.

8. The vaccine composition of claim 7, wherein said antigen comprises a BVDV type 1 or type 2 antigen.

* * * * *